(12) United States Patent
Friedlander et al.

(10) Patent No.: US 7,917,478 B2
(45) Date of Patent: Mar. 29, 2011

(54) SYSTEM AND METHOD FOR QUALITY CONTROL IN HEALTHCARE SETTINGS TO CONTINUOUSLY MONITOR OUTCOMES AND UNDESIRABLE OUTCOMES SUCH AS INFECTIONS, RE-OPERATIONS, EXCESS MORTALITY, AND READMISSIONS

(75) Inventors: Robert R. Friedlander, Southbury, CT (US); Richard A. Hennessy, Austin, TX (US); James R. Kraemer, Sante Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 554 days.

(21) Appl. No.: 11/741,467

(22) Filed: Apr. 27, 2007

(65) Prior Publication Data

US 2008/0208813 A1 Aug. 28, 2008

Related U.S. Application Data

(63) Continuation-in-part of application No. 11/678,959, filed on Feb. 26, 2007, now Pat. No. 7,752,154.

(51) Int. Cl.
G06F 7/00 (2006.01)

(52) U.S. Cl. ............ 707/688; 707/694; 707/736; 706/47

(58) Field of Classification Search ................ 707/3, 10, 707/104.1, 203, 999.002, 999.004, 999.102, 707/999.104, 688, 694, 736; 706/47
See application file for complete search history.

(56) References Cited

U.S. PATENT DOCUMENTS

| | | | | |
|---|---|---|---|---|
| 4,890,227 A | | 12/1989 | Watanabe et al. | |
| 5,070,453 A | | 12/1991 | Duffany | |
| 5,128,871 A | | 7/1992 | Schmitz | |
| 5,212,788 A | * | 5/1993 | Lomet et al. | 1/1 |
| 5,517,642 A | * | 5/1996 | Bezek et al. | 1/1 |
| 5,546,580 A | * | 8/1996 | Seliger et al. | 1/1 |
| 5,696,964 A | * | 12/1997 | Cox et al. | 1/1 |
| 5,764,740 A | | 6/1998 | Holender | |
| 5,838,918 A | | 11/1998 | Prager et al. | |
| 5,880,598 A | | 3/1999 | Duong | |
| 6,021,403 A | | 2/2000 | Horvitz et al. | |
| 6,076,166 A | | 6/2000 | Moshfeghi et al. | |
| 6,212,524 B1 | | 4/2001 | Weissman et al. | |

(Continued)

OTHER PUBLICATIONS

U.S. Appl. No. 11/678,959, filed Feb. 26, 2007, Friedlander et al.

(Continued)

*Primary Examiner* — Eliyah S Harper

(74) *Attorney, Agent, or Firm* — Yee & Associates, P.C.; John R. Pivnichny

(57) ABSTRACT

A method for inferring a probability of a first inference. The inference is related to identification of a cause of an outcome in a healthcare setting. A fact, related to the query, is related to the healthcare setting. The fact further relates to a network of interactions associated with the outcome. Each datum of the database conforms to the dimensions of the database. Each datum of the plurality of data has associated metadata and an associated key. The associated metadata includes data regarding cohorts associated with the corresponding datum, data regarding hierarchies associated with the corresponding datum, data regarding a corresponding source of the datum, and data regarding probabilities associated with integrity, reliability, and importance of each associated datum. The query establishes a frame of reference for the search. The database returns a probability of the correctness of the first inference based on the query and on the data.

20 Claims, 14 Drawing Sheets

U.S. PATENT DOCUMENTS

| | | | |
|---|---|---|---|
| 6,321,207 B1 | 11/2001 | Ye | |
| 6,470,298 B1* | 10/2002 | Banks et al. | 702/181 |
| 6,484,155 B1 | 11/2002 | Kiss et al. | |
| 6,611,846 B1* | 8/2003 | Stoodley | 707/740 |
| 6,675,159 B1 | 1/2004 | Lin et al. | |
| 6,905,816 B2 | 6/2005 | Jacobs et al. | |
| 6,937,147 B2 | 8/2005 | Dilbeck et al. | |
| 6,954,736 B2 | 10/2005 | Menninger et al. | |
| 7,139,675 B2* | 11/2006 | Banks et al. | 702/181 |
| 7,181,428 B2 | 2/2007 | Lawrence | |
| 7,213,009 B2 | 5/2007 | Pestotnik et al. | |
| 7,295,925 B2 | 11/2007 | Breed et al. | |
| 7,356,416 B2* | 4/2008 | Busa | 702/19 |
| 7,403,922 B1 | 7/2008 | Lewis et al. | |
| 7,426,441 B2* | 9/2008 | Mendrick et al. | 702/19 |
| 7,428,554 B1* | 9/2008 | Coberley et al. | 1/1 |
| 7,529,685 B2* | 5/2009 | Davies et al. | 705/3 |
| 7,543,149 B2* | 6/2009 | Ricciardi et al. | 713/176 |
| 7,630,986 B1* | 12/2009 | Herz et al. | 1/1 |
| 2002/0002559 A1* | 1/2002 | Busa | 707/104.1 |
| 2002/0052756 A1 | 5/2002 | Lomangino | |
| 2002/0111922 A1 | 8/2002 | Young et al. | |
| 2002/0156763 A1* | 10/2002 | Marchisio | 707/1 |
| 2003/0018633 A1* | 1/2003 | Horn | 707/4 |
| 2003/0140063 A1 | 7/2003 | Pizzorno et al. | |
| 2003/0177038 A1 | 9/2003 | Rao | |
| 2003/0182310 A1* | 9/2003 | Charnock et al. | 707/104.1 |
| 2004/0006694 A1 | 1/2004 | Heelan et al. | |
| 2004/0122787 A1 | 6/2004 | Avinash et al. | |
| 2005/0004823 A1 | 1/2005 | Hnatio | |
| 2005/0038608 A1 | 2/2005 | Chandra et al. | |
| 2005/0050030 A1* | 3/2005 | Gudbjartsson et al. | 707/3 |
| 2005/0105775 A1* | 5/2005 | Luo et al. | 382/115 |
| 2005/0144062 A1 | 6/2005 | Mittal et al. | |
| 2005/0149466 A1 | 7/2005 | Hale et al. | |
| 2005/0165594 A1 | 7/2005 | Chandra et al. | |
| 2006/0036560 A1 | 2/2006 | Fogel | |
| 2006/0036619 A1* | 2/2006 | Fuerst et al. | 707/100 |
| 2006/0069514 A1 | 3/2006 | Chow et al. | |
| 2006/0155627 A1 | 7/2006 | Horowitz | |
| 2006/0200435 A1 | 9/2006 | Flinn et al. | |
| 2006/0241981 A1* | 10/2006 | Walker | 705/4 |
| 2006/0253418 A1* | 11/2006 | Charnock et al. | 707/1 |
| 2007/0005646 A1* | 1/2007 | Dumais et al. | 707/104.1 |
| 2007/0033084 A1* | 2/2007 | Mascarenhas | 705/7 |
| 2007/0073654 A1 | 3/2007 | Chow et al. | |
| 2007/0073754 A1 | 3/2007 | Friedlander et al. | |
| 2007/0106478 A1* | 5/2007 | Jung et al. | 702/19 |
| 2007/0106754 A1* | 5/2007 | Moore | 709/217 |
| 2007/0136429 A1* | 6/2007 | Fine et al. | 709/206 |
| 2007/0174090 A1 | 7/2007 | Friedlander et al. | |
| 2007/0174091 A1 | 7/2007 | Friedlander et al. | |
| 2007/0174252 A1* | 7/2007 | Rawlings et al. | 707/3 |
| 2007/0185737 A1 | 8/2007 | Friedlander et al. | |
| 2007/0203872 A1 | 8/2007 | Flinn et al. | |
| 2007/0233730 A1* | 10/2007 | Johnston | 707/104.1 |
| 2007/0244701 A1 | 10/2007 | Erlanger et al. | |
| 2007/0274337 A1 | 11/2007 | Purpura | |
| 2007/0276851 A1 | 11/2007 | Friedlander et al. | |
| 2007/0294111 A1* | 12/2007 | Settimi | 705/3 |
| 2008/0010254 A1* | 1/2008 | Settimi | 707/3 |
| 2008/0015871 A1 | 1/2008 | Eder | |
| 2008/0065576 A1 | 3/2008 | Friedlander et al. | |
| 2008/0077463 A1 | 3/2008 | Friedlander et al. | |
| 2008/0082356 A1* | 4/2008 | Friedlander et al. | 705/2 |
| 2008/0082374 A1 | 4/2008 | Kennis et al. | |
| 2008/0114779 A1 | 5/2008 | Friedlander et al. | |
| 2008/0172352 A1 | 7/2008 | Friedlander et al. | |
| 2008/0177687 A1 | 7/2008 | Friedlander et al. | |
| 2008/0177688 A1 | 7/2008 | Friedlander et al. | |
| 2008/0208801 A1 | 8/2008 | Friedlander et al. | |
| 2008/0208814 A1 | 8/2008 | Friedlander et al. | |
| 2008/0208832 A1 | 8/2008 | Friedlander et al. | |
| 2008/0208838 A1 | 8/2008 | Friedlander et al. | |
| 2008/0208875 A1 | 8/2008 | Friedlander et al. | |
| 2008/0208902 A1 | 8/2008 | Friedlander et al. | |
| 2008/0208903 A1 | 8/2008 | Friedlander et al. | |
| 2008/0208904 A1 | 8/2008 | Friedlander et al. | |
| 2008/0311574 A1* | 12/2008 | Manne et al. | 435/6 |
| 2009/0228299 A1* | 9/2009 | Kangarloo et al. | 705/2 |

OTHER PUBLICATIONS

"AHRQ Quality Indicators—Patient Safety Indicators—Technical Specifications", Department of Health and Human Services Agency for Healthcare Research and Quality, Version 3.1 (Mar. 12, 2007) pp. 1-107. http:www.qualityindicators.ahrq.gov.

Hayes et al., "Picking Up the Pieces: Utilizing Disaster Recovery Project Management to Improve Readiness and Response Time", IEEE Industry Applications Magazine, Nov./Dec. 2002, pp. 1-10.

Wang et al., "A Mathematical Approach to Disaster Recovery Planning", Xidian University, National Info Security Engineering and Technology Research Center, Beijing, China, Proceedings of the First International Conference of Semantics, Knowledge, and Grid, SKG 2005, pp. 1-3.

Silver, E.A., "An Overview of Heuristic Solution Methods", The Journal of the Operational Research Society, vol. 55, No. 9, Sep. 2004, pp. 936-956.

Chen et al., "Research on Organization Method of Development Activities for Complicated Product", The 9th International Conference on Computer Supported Cooperative Work in Design Proceedings, vol. 1, May 24-26, 2005, pp. 234-239.

Cao et al., "Research on Resource Scheduling for Development Process of Complicated Product", The 9th International Conference on Computer Supported Cooperative Work in Design Proceedings, vol. 1, May 24-26, 2005, pp. 229-331.

Altmann et al., "Cooperative Software Development: Concepts, Model and Tools", C Doppler Laboratory for Software Engineering, Johannes Kepler University, Linz, 1999, pp. 194-207.

Souder, William E., "Analytical Effectiveness of Mathematical Models for R&D Project Selection", Management Science, Application Series, vol. 19, No. 8, Apr. 1973, pp. 907-923.

U.S. Appl. No. 11/516,954, filed Sep. 7, 2006, Friedlander et al.
U.S. Appl. No. 11/874,382, filed Oct. 18, 2007, Friedlander et al.
U.S. Appl. No. 12/130,779, filed May 30, 2008, Friedlander et al.
U.S. Appl. No. 12/121,947, filed May 16, 2008, Angell et al.
U.S. Appl. No. 12/135,972, filed Jun. 9, 2008, Angell et al.
U.S. Appl. No. 12/135,960, filed Jun. 9, 2008, Angell et al.
U.S. Appl. No. 12/243,825, filed Oct. 1, 2008, Angell et al.

Luckham et al., "Event Processing Glossary", May 2008, Retrieved Jun. 9, 2008, pp. 1-13, <http://complexevents.com/?p=361>.

* cited by examiner

SYSTEM AND METHOD FOR QUALITY CONTROL IN HEALTHCARE SETTINGS TO CONTINUOUSLY MONITOR OUTCOMES AND UNDESIRABLE OUTCOMES SUCH AS INFECTIONS, RE-OPERATIONS, EXCESS MORTALITY, AND READMISSIONS

RELATED APPLICATION

This application is a continuation-in-part of patent application U.S. Ser. No. 11/678,959, filed Feb. 26, 2007, now U.S. Pat. No. 7,752,154 titled "System and Method for Deriving a Hierarchical Event Based Database Optimized for Analysis of Criminal and Security Information".

BACKGROUND OF THE INVENTION

1. Field of the Invention

The present invention relates generally to an improved data processing system and in particular to a method and apparatus for searching data. More particularly, the present invention relates to a computer implemented method, apparatus, and a computer usable program product for an event-based database for analyzing security information to discover past, present, or future potentially criminal activities.

2. Description of the Related Art

Combating terrorism and crime effectively often depends on accurate information. For example, if the location or exact identity of a terrorist or criminal is not known, then apprehending the terrorist or criminal is difficult, if not impossible. Thus, methods and devices for better acquiring and processing information are always desired in the areas of law enforcement and the military.

Finding anomalous criminal or terrorist activities in a sea of information is extraordinarily difficult under the best of circumstances. Pertinent information is often buried in vast quantities of divergent data. Divergent data is sets of data having different types, sizes, compatibilities, and other differences. The data is often of widely different types scattered across various physical systems belonging to different organizations or individuals. Many of the data types, such as picture files, video files, and audio files, are not normally susceptible to normal query techniques. Relevant information is often spread through different points in time. The data is stored often at different levels of granularity; that is, some data has a great deal of associated information while other data has only a little associated information.

Additionally, the data often reflect parts of larger patterns. A first set of data, by itself, is of little value, but together with other data combinations of the first set of data and other data would show a pattern of criminal or terrorist activity. Similarly, patterns or events are often discernable only by piecing together data from multiple individuals or cohorts spread throughout the data. Cohorts are groups of objects or people that share common characteristics or are otherwise part of a group.

To make matters more difficult, not all data is accessible to the individuals to whom the data would matter most. For example, a city detective might not have access to databases of the Federal Bureau of Investigation or the Central Intelligence Agency. Thus, the city detective might not have access to information critical to solving a crime or disrupting a terrorist plot. Similarly, lack of a longitudinal view of criminal or security related events hampers the ability of law enforcement personnel, military personnel, or intelligence analysts from making important inferences that would solve crimes or prevent nefarious activities. Furthermore, much of the available data is subjective or ambiguous.

Databases, data processing systems, and information processing systems have been proposed to attempt to address this problem. However, all known information processing systems suffer from critical flaws, such as in the lack of an ability to deal with data at different levels of granularity, or the lack of the ability to compare divergent data and assign multiple levels of granularity and probability to inferences that can be made from the divergent data.

SUMMARY OF THE INVENTION

Illustrative embodiments provide a computer implemented method, apparatus, and computer usable program code for inferring a probability of a first inference related to identification of a cause of an outcome in a healthcare setting. The method includes receiving at a database regarding a fact related to the healthcare setting. The fact further relates to a network of interactions associated with the outcome. The first inference is absent from the database. The database includes a plurality of divergent data. The plurality of divergent data includes a plurality of cohort data. Each datum of the database is conformed to the dimensions of the database. Each datum of the plurality of data has associated metadata and an associated key. The associated metadata includes data regarding cohorts associated with the corresponding datum, data regarding hierarchies associated with the corresponding datum, data regarding a corresponding source of the datum, and data regarding probabilities associated with integrity, reliability, and importance of each associated datum. The method further includes establishing the fact as a frame of reference for the query and applying a first set of rules to the query. The set of rules are determined for the query according to a second set of rules. The first set of rules determine how the plurality of data are to be compared to the fact. The first set of rules determine a search space. The method also includes executing the query to create the probability of the first inference. The probability of the first inference is determined from comparing the plurality of data according to the first set of rules. The method also includes storing the probability of the first inference.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE PREFERRED EMBODIMENT

Figure 1:
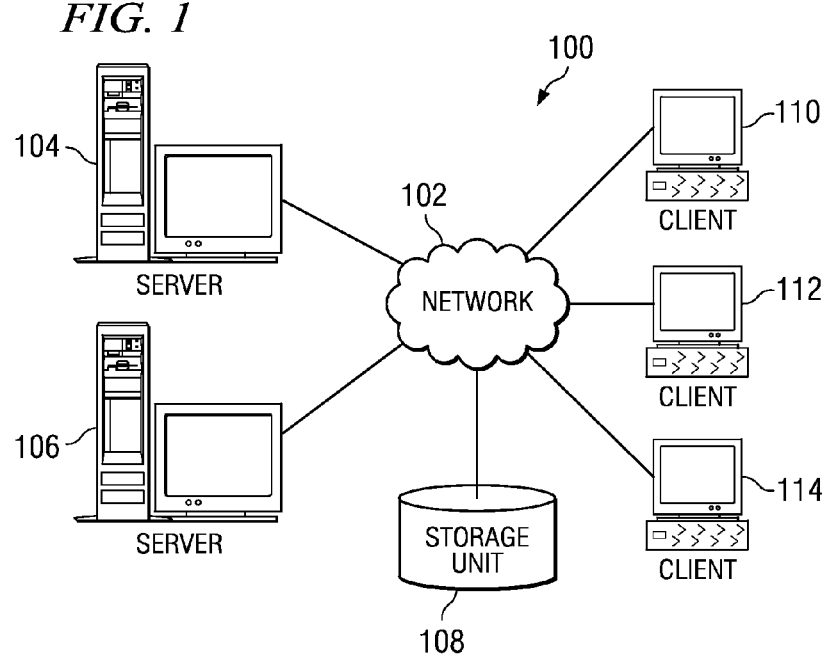
FIG. 1 is pictorial representation of a data processing system in which the aspects of the present invention may be implemented.
Figure 2:
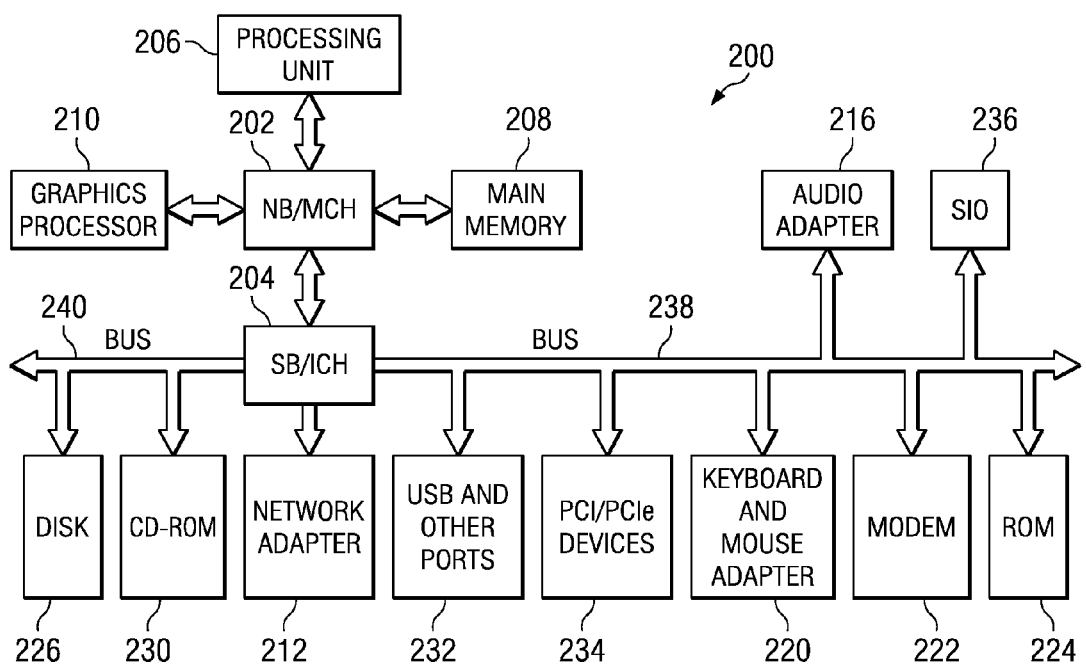
FIG. 2 is a block diagram of a data processing system in which aspects of the present invention may be implemented.

With reference now to the figures and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

With reference now to the figures, FIG. 1 depicts a pictorial representation of a network of data processing systems in which illustrative embodiments may be implemented. Network data processing system 100 is a network of computers in which embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. These clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for different embodiments.

With reference now to FIG. 2, a block diagram of a data processing system is shown in which illustrative embodiments may be implemented. Data processing system 200 is an example of a computer, such as server 104 or client 110 in FIG. 1, in which computer usable code or instructions implementing the processes may be located for the illustrative embodiments.

In the depicted example, data processing system 200 employs a hub architecture including a north bridge and memory controller hub (MCH) 202 and a south bridge and input/output (I/O) controller hub (ICH) 204. Processor 206, main memory 208, and graphics processor 210 are coupled to north bridge and memory controller hub 202. Graphics processor 210 may be coupled to the MCH through an accelerated graphics port (AGP), for example.

In the depicted example, local area network (LAN) adapter 212 is coupled to south bridge and I/O controller hub 204 and audio adapter 216, keyboard and mouse adapter 220, modem 222, read only memory (ROM) 224, universal serial bus (USB) ports and other communications ports 232, and PCI/PCIe devices 234 are coupled to south bridge and I/O controller hub 204 through bus 238, and hard disk drive (HDD) 226 and CD-ROM drive 230 are coupled to south bridge and I/O controller hub 204 through bus 240. PCI/PCIe devices may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM drive 230 may use, for example, an integrated drive electronics (IDE) or serial advanced technology attachment (SATA) interface. A super I/O (SIO) device 236 may be coupled to south bridge and I/O controller hub 204.

An operating system runs on processor 206 and coordinates and provides control of various components within data processing system 200 in FIG. 2. The operating system may be a commercially available operating system such as Microsoft® Windows® XP (Microsoft and Windows are trademarks of Microsoft Corporation in the United States, other countries, or both). An object oriented programming system, such as the Java™ programming system, may run in conjunction with the operating system and provides calls to the operating system from Java programs or applications executing on data processing system 200 (Java and all Java-based trademarks are trademarks of Sun Microsystems, Inc. in the United States, other countries, or both).

Instructions for the operating system, the object-oriented programming system, and applications or programs are located on storage devices, such as hard disk drive 226, and may be loaded into main memory 208 for execution by processor 206. The processes of the illustrative embodiments may be performed by processor 206 using computer implemented instructions, which may be located in a memory such as, for example, main memory 208, read only memory 224, or in one or more peripheral devices.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. Also, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may be comprised of one or more buses, such as a system bus, an I/O bus and a PCI bus. Of course the bus system may be implemented using any type of communications fabric or architecture that provides for a transfer of data between different components or devices attached to the fabric or architecture. A communications unit may include one or more devices used to transmit and receive data, such as a modem or a network adapter. A memory may be, for example, main memory 208 or a cache such as found in north bridge and memory controller hub 202. A processing unit may include one or more processors or CPUs. The depicted examples in FIGS. 1-2 and above-described examples are not meant to imply architectural limitations. For example, data processing system 200 also may be a tablet computer, laptop computer, or telephone device in addition to taking the form of a PDA.

Illustrative embodiments provide a computer implemented method, apparatus, and computer usable program code for creating and using a centralized database for managing information. The centralized database can be used to derive probabilities of inferences based on comparison of data within the centralized database according to a set of search rules. The search rules are, themselves, determined by a set of determination rules. Thus, the system prevents the entirety of the data in the database from being compared in every possible combination in order that limited computing resources can execute desired queries. The system is particularly useful in the context of criminal investigations or intelligence services where vast quantities of data are to be sifted.

Many of the systems, items, or persons shown throughout FIG. 3 through FIG. 19 are similar. Thus, similar reference numerals in these figures refer to similar items.

Figure 3:
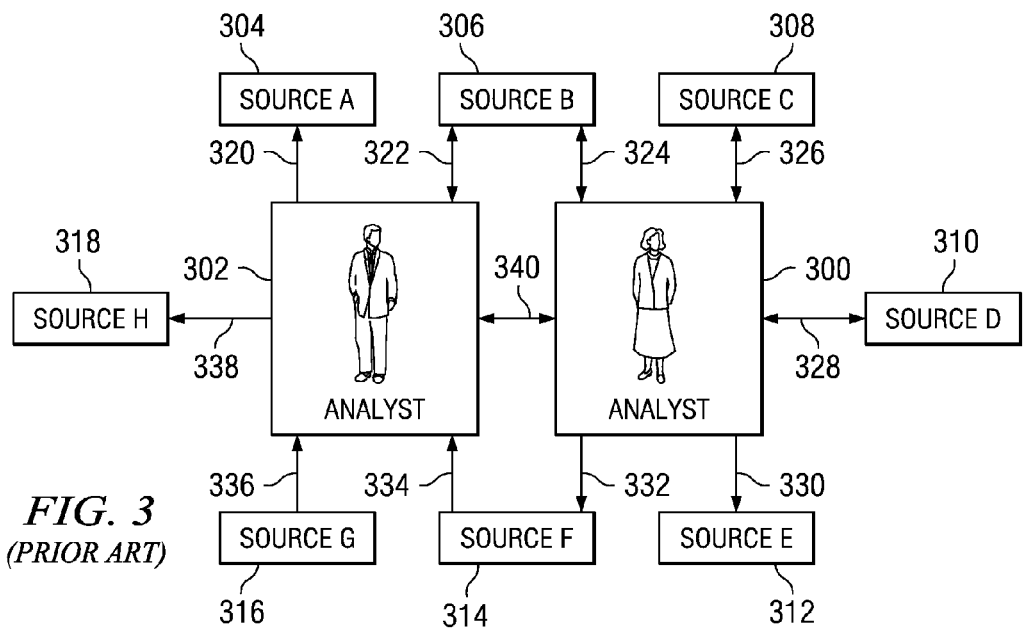
FIG. 3 is a block diagram illustrating a prior art method of analyzing data in an attempt to identify past, present, or future criminal activity.

FIG. 3 is a block diagram illustrating a prior art method of analyzing data in an attempt to identify past, present, or future criminal activity. The prior art method shown can be implemented by one or more users using one or more data processing systems, such as server 104, server 106, client 110, client 112, and client 114 in FIG. 1, and data processing system 200 shown in FIG. 2. These data processing systems can communicate over a network, such as network 102 shown in FIG. 1.

As shown in FIG. 3, analyst 300 and analyst 302 receive information from a variety of sources of information and attempt to derive inferences from the variety of sources of information. Sources of information can be any source of information, such as video camera footage, news accounts, reports from field operatives, police reports, police radio transmissions, voice recordings, or nearly any kind of information source. To show the complexity of the problem, many data sources are shown, such as data source 304, data source 306, data source 308, data source 310, data source 312, data source 314, data source 316, and data source 318. Analyst 300 and analyst 302 also may input data back into some of the data sources.

The arrows show the direction of information from the sources and the analysts. An arrow pointing away from an analyst means that the analyst is able to input data into a source, but not to receive data from the source. An arrow pointing toward an analyst means that the analyst is able to receive data from a source, but not to input data into the source. An arrow pointing both directions indicates that the analyst is able to both input data into the source and receive data from the source.

Thus, for example, analyst 302 can only input data into source 304, as shown by arrow 320. Both analyst 300 and analyst 302 can input data to and receive data from source 306, as shown by arrows 322 and 324. Analyst 300 can both input data into and receive data from source 308, as shown by arrows 326; however, analyst 302 has no access whatsoever to source 308. Similarly, analyst 300 can receive data from and input data to source 310, as shown by arrows 328, while analyst 302 cannot access source 310 at all. Analyst 302 can only input data into source 312, as shown by arrow 330.

Analyst 300 can input data into source 314; however, only analyst 302 can receive data from source 314, as shown by arrows 332 and 334. Analyst 302 can receive data from 316, but cannot input data to source 316, as shown by arrows 336. Analyst 302 can input data to source 318, but cannot receive data from source 318, as shown by arrow 338. Analyst 300 cannot access source 316, source 318, or source 304.

Analyst 300 and analyst 302 can send and receive data from each other. However, because analyst 300 and analyst 302 do not have the same level of access to information, both analysts are subject to blind spots in information and are thus unable to make certain inferences that could be critical to solving a case or even stopping a terrorist attack with weapons of mass destruction.

For example, analyst 300 receives data from source 308 that indicates that Suspect purchased one thousand pounds of high nitrate fertilizer just prior to the planting season in the state of X. Analyst 300 does not consider the purchase to be important because large quantities of high nitrate fertilizer are often purchased at the given time of year.

On the other hand, analyst 302 receives data from source 316 that indicates that Suspect has moved to the state of X. Analyst 302 receives further information from source 314 that Suspect is a member of a criminal organization infamous for bombing government buildings and that Suspect has expert bomb-making skills from military service. Analyst 302 considers the information somewhat important. However, because analyst 302 lacks any other evidence or information, analyst 302 simply inputs into source 318 the fact that Suspect in the state of X.

Combined, the facts that Suspect purchased 1000 pounds of high nitrate fertilizer, that Suspect moved to the state of X, that Suspect is a member of a criminal organization infamous for bombing government buildings, and that Suspect is an expert bomb maker creates an inference that a high degree of probability exists that Suspect intends to engage in criminal or terrorist activities.

However, analyst 300 cannot make this inference because analyst 300 only knows that Suspect purchased high nitrate fertilizer at a time of year when such purchases are normally made. On the other hand, analyst 302 cannot make this inference because analyst 302 does not know that Suspect has purchased a large quantity of high nitrate fertilizer.

Still more problematically, the fact that analyst 300 and analyst 302 can communicate with each other may be of no assistance. Unless by happenstance analyst 300 and analyst 302 discuss these facts together, neither analyst will make the inference that Suspect poses a clear and present danger. However, analyst 300 and analyst 302 are unlikely to discuss the matter because analyst 300 has no reason to believe that the high nitrate fertilizer purchase is abnormal and analyst 302 has no reason to believe that Suspect may be currently engaged in criminal activity.

As a result, Suspect may be able to execute a bomb attack on a government building without prior interference. In retrospect, after an attack, analyst 300 and analyst 302 might be able to infer that together they had the necessary information. However, without the hindsight knowledge of the fact of the attack they probably would be unable to make the inference. While making the inference in hindsight might be valuable to finding and prosecuting Suspect after the attack, law enforcement personnel would prefer to thwart the attack in the first place.

Note that the inference that Suspect is engaging in a plot to build a bomb and then use the bomb in a terrorist activity is not one hundred percent reliable. For all analyst 300 and analyst 302 know, Suspect may have left the criminal organization and mended his ways. To make a living, he became a farmer and has need for the high nitrate fertilizer because the proper time for applying the fertilizer to his crops is at hand. However, the combination of the facts certainly allows for the reasonable inference that a very high probability exists that Suspect is involved in criminal activity. Thus, analyst 300 or analyst 302 would direct other law enforcement personnel to investigate Suspect further to determine if Suspect is actually involved in criminal activity. If Suspect were engaged in criminal activity, then a bomb attack could be thwarted if either analyst 300 or analyst 302 could make the inference.

However, the above-described scenario is very simplistic because this scenario assumes that analyst 300 and analyst 302 received and considered the relevant information in the first place. Because the amount of information available to be analyzed is nearly incomprehensibly vast, neither analyst may have had their attention drawn to any of the facts described above. Thus, the likelihood is high both analysts would be oblivious to the potential threat posed by Suspect. The information necessary to make the inference that Suspect is a threat does exists however, finding that information and then making the proper inference is comparable to finding two needles in millions of different kinds of haystacks, all moving at a high rate of speed.

Figure 4:
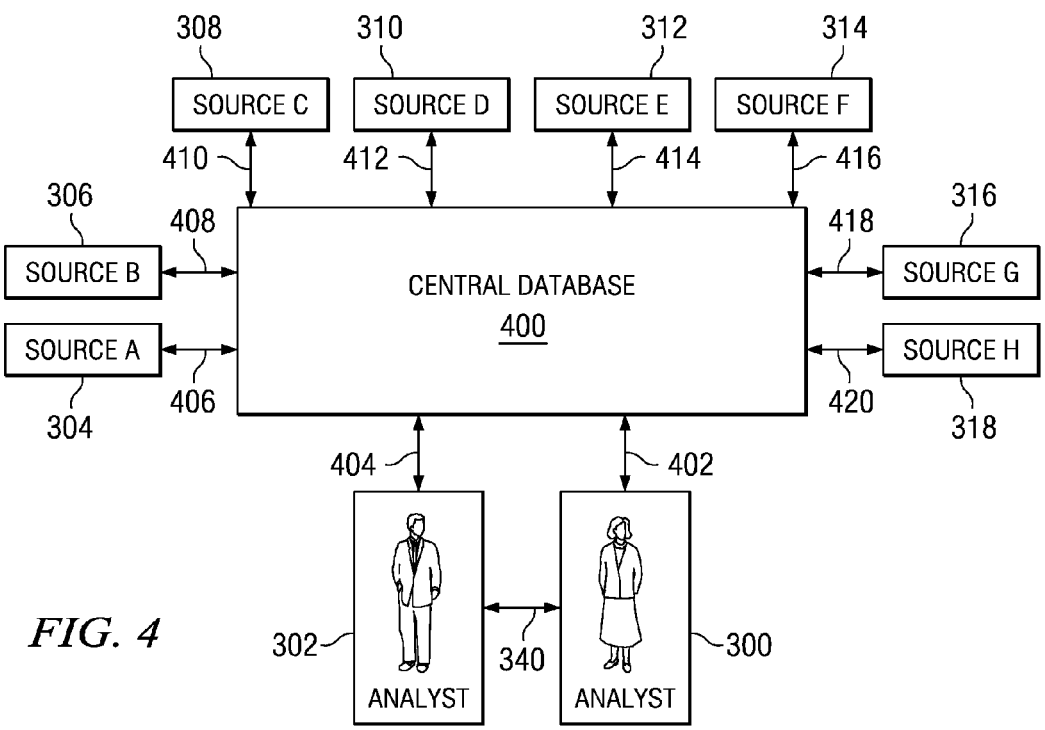
FIG. 4 is a block diagram illustrating a central database used for identifying past, present, or future criminal activity, in accordance with an illustrative embodiment.

FIG. 4 is a block diagram illustrating a central database used for identifying past, present, or future criminal activity, in accordance with an illustrative embodiment. The method shown in FIG. 4 can be implemented by one or more users using one or more data processing systems, such as server 104, server 106, client 110, client 112, and client 114 in FIG. 1 and data processing system 200 shown in FIG. 2, which communicate over a network, such as network 102 shown in FIG. 1. Additionally, the illustrative embodiments described in FIG. 4 and throughout the specification can be implemented using these data processing systems in conjunction with central database 400.

FIG. 4 shows a solution to the problem of allowing different analysts to both find and consider relevant information from a truly massive amount of divergent data. Central database 400 allows analyst 300 and analyst 302 to find relevant information based on one or more queries and, more importantly, cause central database 400 to assign probabilities to the likelihood that certain inferences can be made based on the query. The process is massively recursive in that every piece of information added to the central database causes the process to be re-executed. An entirely different result can arise based on new information. Information can include the fact that the query itself was simply made. Information can also include the results of the query, or information can include data from any one of a number of sources.

Additionally, central database 400 receives as much information as possible from as many different sources as possible. Thus, central database 400 serves as a central repository of information from analyst 300, analyst 302, source 304, source 306, source 308, source 310, source 312, source 314, source 316, and source 318. In an illustrative embodiment, central database 400 can also input data into each of those sources. Arrows 402, arrows 404, arrows 406, arrows 408, arrows 410, arrows 412, arrows 414, arrows 416, arrows 418, and arrows 420 are all bidirectional arrows to indicate that central database 400 is capable of both receiving and inputting information from and to all sources of information. However, not all sources are necessarily capable of receiving data; in these cases, central database 400 does not attempt to input data into the corresponding source.

Continuing the example regarding Suspect, either or both of analyst 300 or analyst 302 could have made the inference that Suspect was possibly engaged in criminal activity by submitting queries to central database 400. Thus, the odds of thwarting an attack by Suspect are greatly increased by the mechanisms and methods of the illustrative embodiments.

Central database 400 is adapted to receive a query regarding a fact, use the query as a frame of reference, use a set of rules to generate a second set of rules to be applied when executing the query, and then execute the query using the second set of rules to compare data in central database 400 to create probability of an inference. The probability of the inference is stored as additional data in the database and is reported to the analyst or analysts submitting the query.

Thus, continuing the above example, analyst 300 submits a query to central database 400 to compare known bomb makers to explosive material purchases. Central database 400 uses these facts or concepts as a frame of reference. A frame of reference is an anchor datum or set of data that is used to limit which data are searched in central database 400. The frame of reference also helps define the search space. The frame of reference also is used to determine to what rules the searched data will be subject. Thus, when the query is executed, sufficient processing power will be available to make inferences.

The frame of reference is used to establish a set of rules for generating a second set of rules. For example, the set of rules could be used to generate a second set of rules that include searching all information related to bombs, all information related to bomb makers, and all information related to purchases of explosive materials and bomb making materials, but no other information. The first set of rules also creates a rule that specifies that only certain interrelationships between these data sets will be searched.

The database uses the second set of rules when the query is executed. In this case, the query compares the relevant data in the described classes of information. In comparing the data from all sources, the query matches purchases of explosive materials to known bomb makers. Central database 400 then produces a probability of an inference. The inference is that Suspect has purchased 1000 pounds of high nitrate fertilizer, a known explosive. Possibly thousands of other inferences matching other bomb makers to purchases of explosives are also made. Thus, the analyst desires to narrow the search because the analyst cannot pick out the information regarding Suspect from the thousands of other inferences.

Continuing the example, this inference and the probability of inference are re-inputted into central database 400 and an additional query is submitted to determine an inference regarding a probability of criminal activity. Again, central database 400 establishes the facts of the query as a frame of reference and then uses a set of rules to determine another set of rules to be applied when executing the query. This time, the query will compare criminal records and group affiliations of all bomb makers identified in the first query. The query will also compare the various identified bomb making materials and their ability to damage buildings, where the identified bomb making materials have been purchased in the identified amounts over a period of time. Thus, if Suspect purchased 100 pounds of high nitrate fertilizer ten times in ten days, this fact could be inferred.

The query is again executed using the second set of rules. The query compares all of the facts and creates a probability of a second inference. In this illustrative example, the probability of a second inference is that a chance between 85 percent and 99 percent exists that Suspect is engaged in a plot to bomb buildings. Analyst 300 then uses this inference to direct law enforcement, military, or other relevant personnel to further investigate Suspect.

Thus, central database 400 includes one or more divergent data. The plurality of divergent data includes a plurality of cohort data. Each datum of the database is conformed to the dimensions of the database. Each datum of the plurality of data has associated metadata and an associated key. A key uniquely identifies an individual datum. A key can be any unique identifier, such as a series of numbers, alphanumeric characters, other characters, or other methods of uniquely identifying objects. The associated metadata includes data regarding cohorts associated with the corresponding datum, data regarding hierarchies associated with the corresponding datum, data regarding a corresponding source of the datum, and data regarding probabilities associated with integrity, reliability, and importance of each associated datum.

Figure 5:
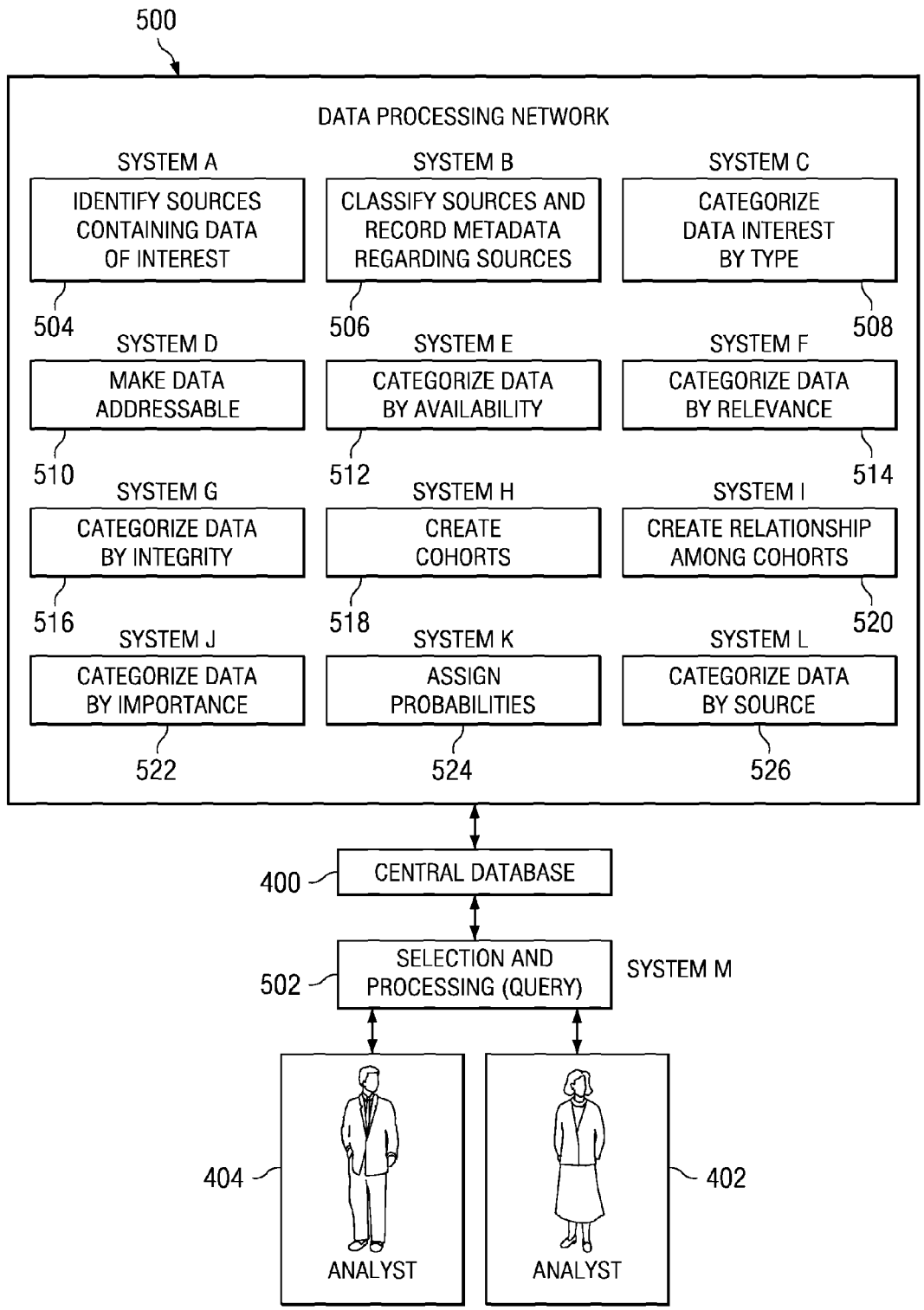
FIG. 5 is a block diagram of a data processing network used in conjunction with a central database for identifying past, present, or future criminal activity, in accordance with an illustrative embodiment.
Figure 18:
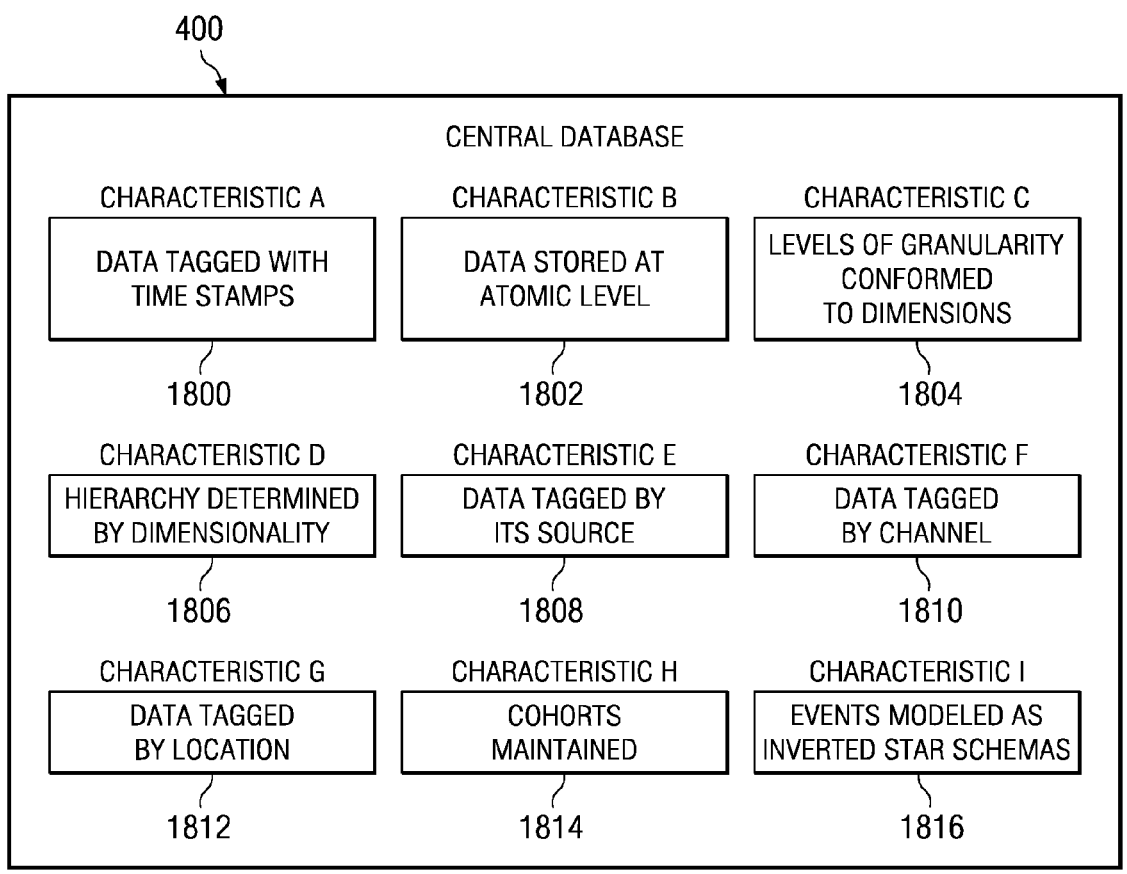
FIG. 18 is a block diagram of illustrating components and operating characteristics of a central database for identifying past, present, or future criminal activity, in accordance with an illustrative embodiment.
Figure 19:
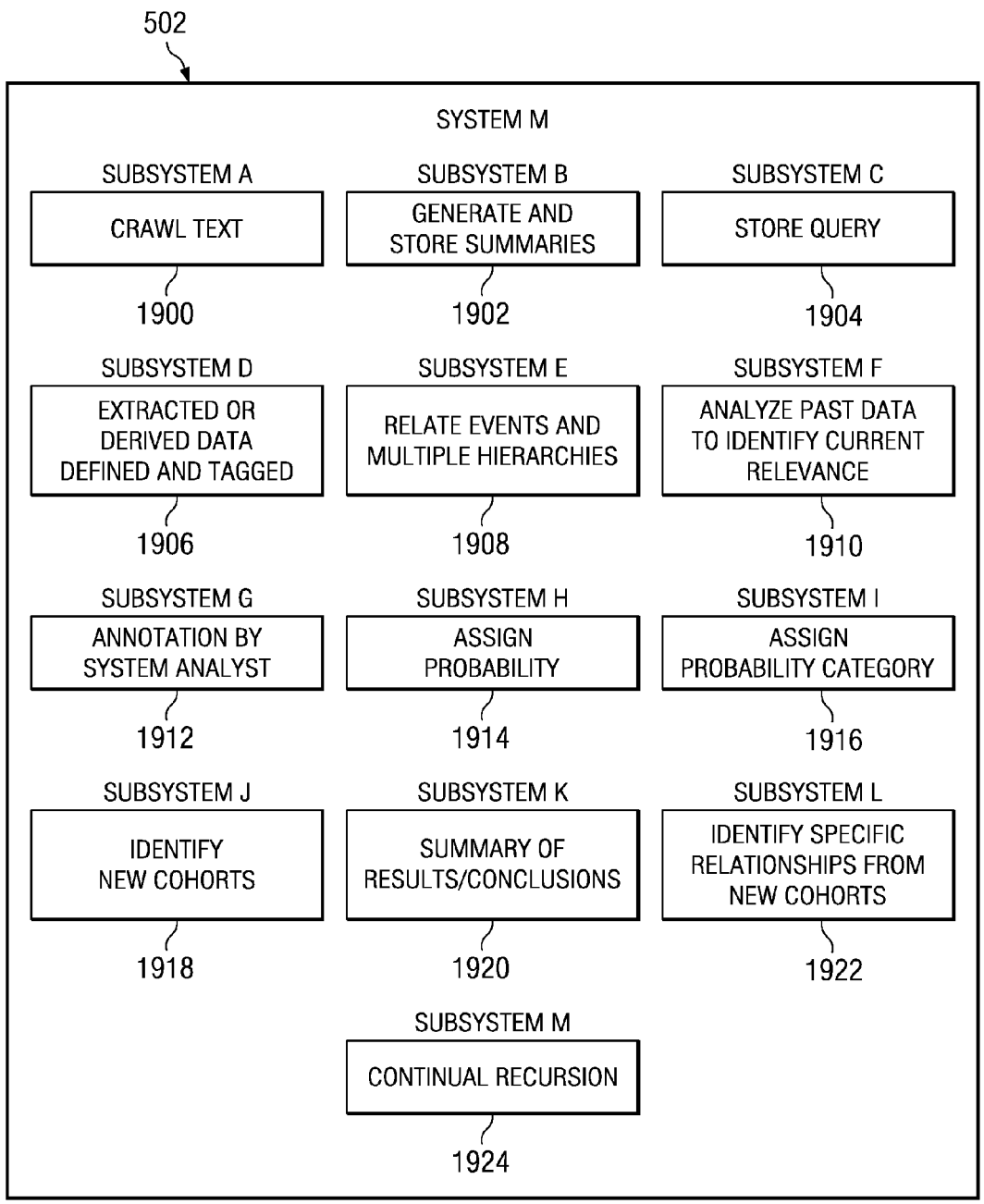
FIG. 19 is a block diagram illustrating subsystems for selection and processing of data using a central database for identifying past, present, or future criminal activity, in accordance with an illustrative embodiment.

Central database 400 is described further with respect to FIG. 5 through FIG. 19. FIG. 5 describes how central database 400 operates. FIG. 6 through FIG. 17 describe additional details regarding how various systems in central database 400 operate. FIG. 18 describes the structure of central database 400. FIG. 19 describes the selection and processing methods and mechanisms used by central database 400 during a query submitted by analysts.

FIG. 5 is a block diagram of a data processing network used in conjunction with a central database for identifying past, present, or future criminal activity, in accordance with an illustrative embodiment. Data processing network 500 can be one or more of a vast number of data processing systems, such as server 104, server 106, client 110, client 112, and client 114 in FIG. 1, and data processing system 200 shown in FIG. 2. These data processing systems can communicate over a network, such as network 102 shown in FIG. 1. Central database 400 in FIG. 4 communicates back and forth with data processing network 500. Central database 400 is accessed using selection and processing rules, represented by System M 502. Queries and possibly additional information are submitted by analyst 300 or analyst 302, shown in FIG. 3, as shown by arrows 402 and 404.

Data processing network 500 includes a number of different systems, each of which performs different functions. Each system shown can be one or more data processing systems connected via a network, as described above. Each system shown in data processing network 500 can also be one or more hardware systems or software programs adapted to perform the functions associated with the corresponding system. More or different systems than those shown can exist in data processing network 500. Those shown are only examples of systems that describe the functions of central database 400.

Examples of systems include system A 504, system B 506, system C 508, system D 510, system E 512, system F 514, system G 516, system H 518, system 1520, system J 522, system K 524, and system L 526. Additionally, System M 502 can itself be considered a system, designated system M 502. System M 502 is described in more detail with respect to FIG. 19.

System A 504 is a system for identifying sources of data containing data of interest. System B 506 is a system for classifying sources of data and for recording metadata regarding the sources. As described below, central database 400 stores all data at the finest level possible, known as individual datum, and associates metadata and an identification key with each datum. System B 506 is the system that deals with this function.

System C 508 is a system for categorizing data of interest by type. System D 510 is a system for making data addressable. System E 512 is a system for categorizing data by availability. System F 514 is a system for categorizing data by relevance. System G 516 is a system for categorizing data by integrity. System H 518 is a system for creating cohorts. System 1520 is a system for creating relationships among cohorts. A cohort is a group of associated individuals or objects. A cohort can be treated as a single entity; thus, central database 400 can effectively find cohorts of interest. Additional queries can "drill down" and find sub-cohorts of further interest. The process is repeatable until specific individuals or objects are found.

System J 522 is a system for categorizing data by importance. System K 524 is a system for assigning probabilities to inferences and assigning probabilities to the trustworthiness, reliability, importance, and integrity of individual datum. System L 526 is a system for categorizing data by the source of the data.

Figure 6:
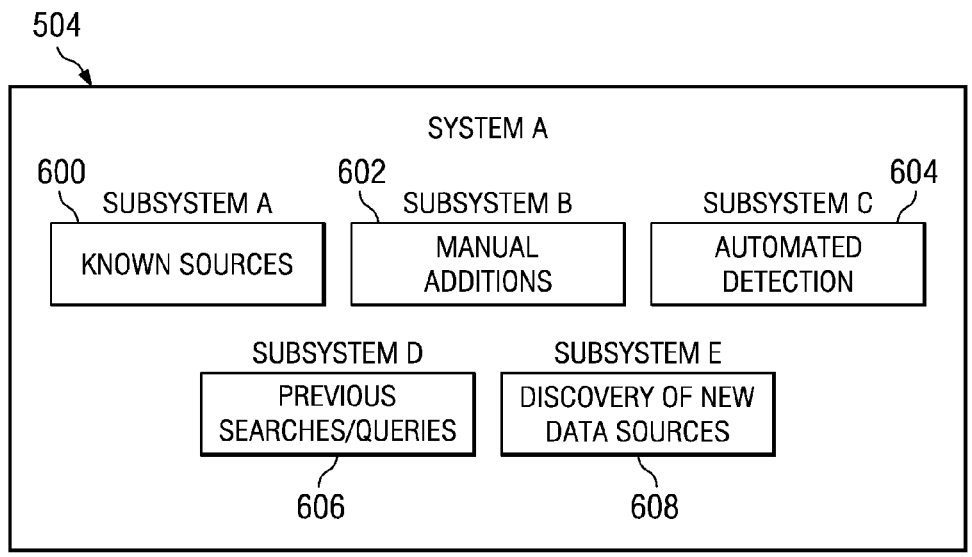
FIG. 6 is a block diagram illustrating functions of a data processing system used with a data processing network and a central database for identifying past, present, or future criminal activity, in accordance with an illustrative embodiment.

FIG. 6 is a block diagram illustrating functions of a data processing system used with a data processing network and a central database for identifying past, present, or future criminal activity, in accordance with an illustrative embodiment. Specifically, FIG. 6 illustrates additional details regarding system A 504 in FIG. 5. System A 504 of FIG. 6 can be implemented via one or more data processing systems connected by a network, as described in FIGS. 1 and 2, or via one or more hardware systems or software programs that can perform the functions of system A 504. System A 504 of FIG. 6 is used in conjunction with other systems and functions of data processing network 500 to allow central database 400 of FIG. 5 to effectively receive and process queries to create probabilities of inferences. System A 504 includes a number of subsystems implemented as one or more hardware or software systems in one or more data processing systems.

Many data sources exist and many new data sources are created nearly continuously. System A 504 is used to find new and existing sources of data. Examples of systems for finding data of interest include web crawlers, software or hardware for checking or updating known sources of information, software or hardware for receiving user-defined information, software or hardware for performing data mining, and any number of additional sources of information.

System A 504 can receive data from various sources, such as known sources from subsystem A 600, manual additions of information from subsystem B 602, automated detection of information from subsystem C 604, previous searches and queries from subsystem D 606, and through the discovery of new data sources from subsystem E 608. System A 504 continually checks for new data sources and updates to known data sources.

Figure 7:
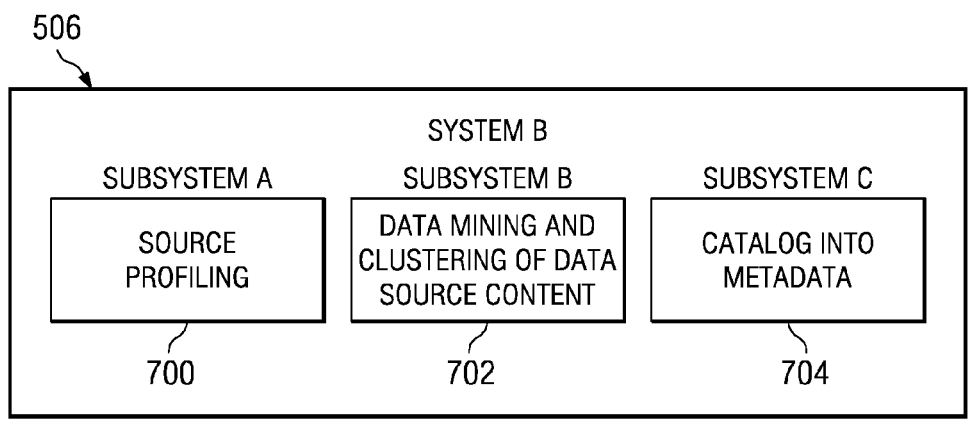
FIG. 7 is a block diagram illustrating functions of a data processing system used with a data processing network and a central database for identifying past, present, or future criminal activity, in accordance with an illustrative embodiment.

FIG. 7 is a block diagram illustrating functions of a data processing system used with a data processing network and a central database for identifying past, present, or future criminal activity, in accordance with an illustrative embodiment. Specifically, FIG. 7 illustrates additional details regarding system B 506 in FIG. 5. System B 506 of FIG. 7 can be implemented via one or more data processing systems connected by a network, as described in FIGS. 1 and 2, or via one or more hardware systems or software programs that can perform the functions of system B 506. System B 506 of FIG. 7 is used in conjunction with other systems and functions of data processing network 500 to allow central database 400 of FIG. 5 to effectively receive and process queries to create probabilities of inferences. System B 506 includes a number of subsystems implemented as one or more hardware or software systems in one or more data processing systems.

System B 506 classifies sources and records metadata regarding each source. Classification of sources into various levels of classifications assists central database 400 in FIG. 4 and data processing network 500 in FIG. 5 to effectively group information together. To further these functions, subsystem A 700 performs source profiling. Source profiling includes one or more of describing the location of the source of information, the trustworthiness of the source, the reliability of the source, the integrity of the source, the time the source was available, the time the source was last updated, contact information regarding the source, or many other types of information regarding the source of data.

System B 506 also includes subsystem B 702 for performing data mining and clustering of data source content. Subsystem B 702 allows system B 506 to mine data from various sources and then cluster the data according to various parameters, such as data source, data type, time stamps associated with the data, data having similar subject matter, data category, and many other subjects about which data can be clustered. System B 506 also includes subsystem C 704 for cataloging data within a source into metadata. This software or hardware allows system B 506 to establish metadata for each datum and associate the metadata with the datum.

An example of software that can implement system B 506 is the Unstructured Information Management Architecture (UIMA) platform available from International Business Machines corporation of Armonk, N.Y. UIMA can also be implemented as hardware. Clustering can also be performed using a clustering algorithm, Baysian statistics, user-defined rules, or combinations of these techniques.

Figure 8:
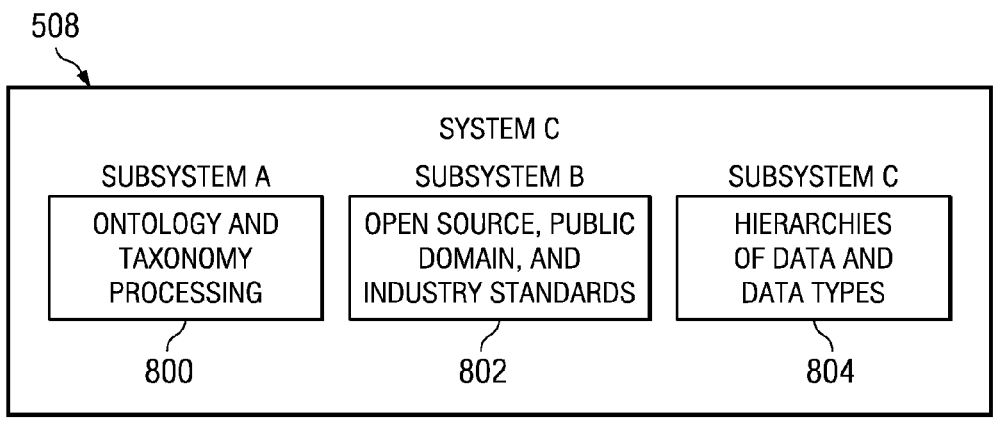
FIG. 8 is a block diagram illustrating functions of a data processing system used with a data processing network and a central database for identifying past, present, or future criminal activity, in accordance with an illustrative embodiment.

FIG. 8 is a block diagram illustrating functions of a data processing system used with a data processing network and a central database for identifying past, present, or future criminal activity, in accordance with an illustrative embodiment. Specifically, FIG. 8 illustrates additional details regarding system C 508 in FIG. 5. System C 508 of FIG. 8 can be implemented via one or more data processing systems connected by a network, as described in FIGS. 1 and 2, or via one or more hardware systems or software programs that can perform the functions of system C 508. System C 508 of FIG. 8 is used in conjunction with other systems and functions of data processing network 500 to allow central database 400 of FIG. 5 to effectively receive and process queries to create probabilities of inferences. System C 508 includes a number of subsystems implemented as one or more hardware or software systems in one or more data processing systems.

System C 508 categorizes data of interest by type. System C 508 includes subsystem A 800 for performing ontology and taxonomy processing of data in order to categorize data of interest by type. Subsystem B 802 also categorizes data of interest by type according to open source, public domain, and industry standards. Additionally, subsystem C 804 categorizes data of interest by type according to hierarchies of data and data types established in system B 506.

Figure 9:
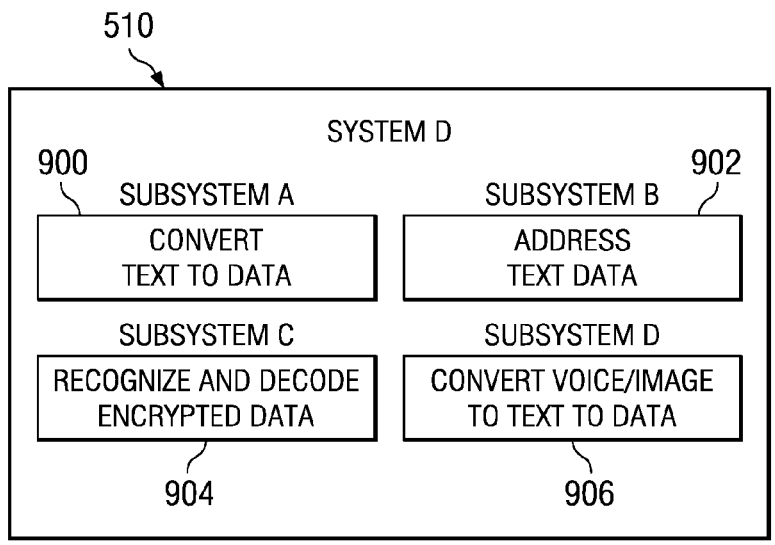
FIG. 9 is a block diagram illustrating functions of a data processing system used with a data processing network and a central database for identifying past, present, or future criminal activity, in accordance with an illustrative embodiment.

FIG. 9 is a block diagram illustrating functions of a data processing system used with a data processing network and a central database for identifying past, present, or future criminal activity, in accordance with an illustrative embodiment. Specifically, FIG. 9 illustrates additional details regarding system D 510 in FIG. 5. System D 510 of FIG. 9 can be implemented via one or more data processing systems connected by a network, as described in FIGS. 1 and 2, or via one or more hardware systems or software programs that can perform the functions of system D 510. System D 510 of FIG. 9 is used in conjunction with other systems and functions of data processing network 500 to allow central database 400 of FIG. 5 to effectively receive and process queries to create probabilities of inferences. System D 510 includes a number of subsystems implemented as one or more hardware or software systems in one or more data processing systems.

System D 510 makes data addressable. Addressability of data allows data to be stored at an atomic level. Such data is considered atomic data. Atomic data is data stored at the finest possible degree of granularity. Thus, for example, data regarding a person is not necessarily stored under a person's name. Instead, data regarding the person is stored separately as name, address, phone number, and other information regarding the person. Each fact is stored as an individual datum. Metadata associated with each datum allows central database 400 in FIG. 4 and data processing network 500 in FIG. 5 to associate a number of individual data with each other in order to build a profile of the person.

The profile of the person could be considered a cohort. Cohorts are groups of objects or people that share common characteristics or are otherwise part of a group. Thus, the name, address, phone number, and other information regarding an individual can be associated with that individual. The cohort is the individual in that all of the individual facts regarding the individual are associated with that individual.

Making atomic data addressable is a non-trivial task, because most data received at central database 400 in FIG. 4 or data processing network 500 in FIG. 5 is not atomic and is not easily addressable. Thus, system D 510 includes subsystem A 900 for converting text to data. Similarly, system D 510 includes subsystem B 902 for addressing text data derived from subsystem A 900. System D 510 also includes subsystem C 904 for recognizing and decoding encrypted data. If the data cannot be decrypted, then subsystem C 904 can recognizing encrypted data and store the fact that the encrypted data exists, along with any information known about the encrypted data, such as source, time of creation, time of entry, encryption method if known, or other information.

Additionally, system D 510 includes subsystem D 906 for converting voice or image files to text, and from there converting text to data. Subsystem B 902 can then allow such data generated in subsystem D 906 to be made addressable at the atomic level.

Figure 10:
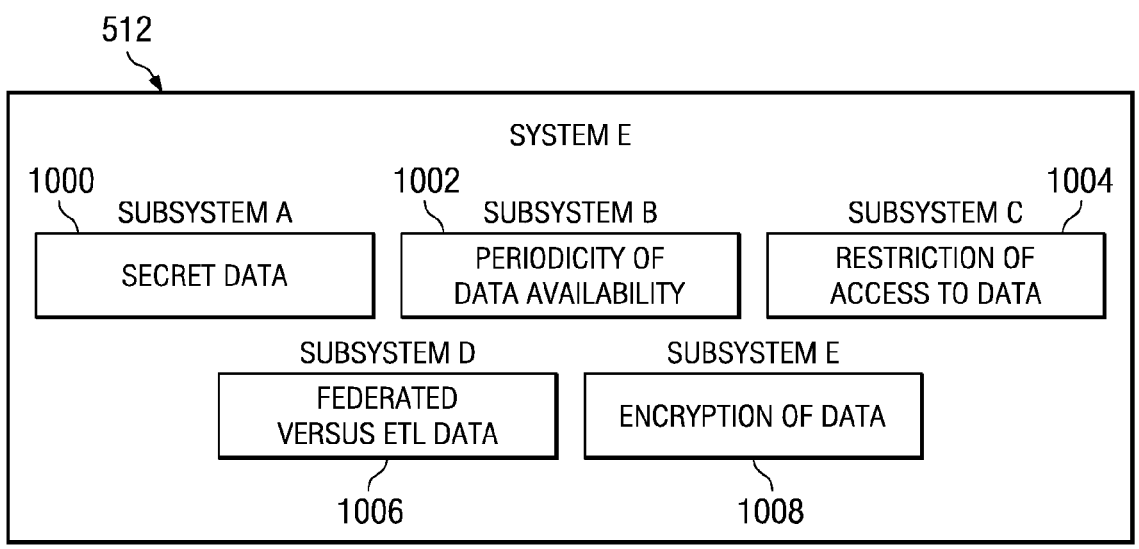
FIG. 10 is a block diagram illustrating functions of a data processing system used with a data processing network and a central database for identifying past, present, or future criminal activity, in accordance with an illustrative embodiment.

FIG. 10 is a block diagram illustrating functions of a data processing system used with a data processing network and a central database for identifying past, present, or future criminal activity, in accordance with an illustrative embodiment. Specifically, FIG. 10 illustrates additional details regarding system E 512 in FIG. 5. System E 512 of FIG. 10 can be implemented via one or more data processing systems connected by a network, as described in FIGS. 1 and 2, or via one or more hardware systems or software programs that can perform the functions of system E 512. System E 512 of FIG. 10 is used in conjunction with other systems and functions of data processing network 500 to allow central database 400 of FIG. 5 to effectively receive and process queries to create probabilities of inferences. System E 512 includes a number of subsystems implemented as one or more hardware or software systems in one or more data processing systems.

System E 512 categorizes data by availability. Data might be recognized, but not necessarily available. Data should be categorized by availability in order to understand the context of data that is available. Thus, for example, system E 512 includes subsystem A 1000 for determining and recording whether data is secret data. Similarly, system E 512 includes subsystem B 1002 for determining the periodicity of data availability. Some data may be available at only particular times or time intervals. Similarly, system E 512 includes subsystem C 1004 for identifying and recording restriction of access to data and subsystem E 1008 for identifying and recording the encryption of data.

System E 512 also includes subsystem D 1006 determining whether data should be federated or accessed via extract, transform, and load (ETL) techniques. The decision of whether data should be made available via federation or extract, transform, and load techniques can be important. Federated access to data is made by accessing desired data piecemeal. Extract, transform, and load techniques allow access to data by extracting, transforming, and loading all data onto a local network or data processing system.

For example, a large database is stored at a building maintained by the Federal Bureau of Investigation. A remote computer can access the database over a network via a query to determine various information about a known suspect. This type of access to the data in the database is federated data access. On the other hand, the entire database could be extracted, transformed, and loaded onto what was the remote computer or remote network. The formerly remote computer can now access the information about the known suspect directly without accessing the database stored at the building maintained by the Federal Bureau of Investigation.

The decision as to whether efficient access to data is accomplished via federation or extract, transform, and load techniques can be difficult. Techniques for efficiently making this decision are found in our disclosure identified by application Ser. No. 11/416,973 filed on May 2, 2006.

Figure 11:
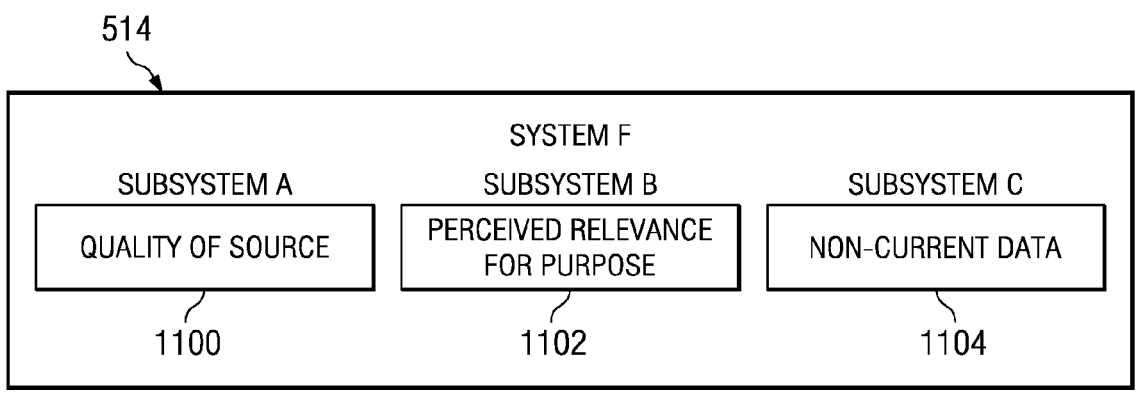
FIG. 11 is a block diagram illustrating functions of a data processing system used with a data processing network and a central database for identifying past, present, or future criminal activity, in accordance with an illustrative embodiment.

FIG. 11 is a block diagram illustrating functions of a data processing system used with a data processing network and a central database for identifying past, present, or future criminal activity, in accordance with an illustrative embodiment. Specifically, FIG. 11 illustrates additional details regarding system F 514 in FIG. 5. System F 514 of FIG. 11 can be implemented via one or more data processing systems connected by a network, as described in FIGS. 1 and 2, or via one or more hardware systems or software programs that can perform the functions of system F 514. System F 514 of FIG. 11 is used in conjunction with other systems and functions of data processing network 500 to allow central database 400 of FIG. 5 to effectively receive and process queries to create probabilities of inferences. System F 514 includes a number of subsystems implemented as one or more hardware or software systems in one or more data processing systems.

System F 514 categorizes data by relevance. System F 514 includes subsystem A 1100 for determining a quality of a source of data and categorizing the data from that source based on the quality of the source. The quality of the source of data has an impact on the relevance of the data in that low quality data will be less relevant. Low quality data is less relevant because the data is less reliable, and data that is less reliable is less relevant. The quality of the source of data can be implemented quantitatively, through assigning a number scale to the quality of data, or qualitative, as in assigning a quality level such as "low," "medium," and "high." Data can be categorized by quality; thus, data of a given quality from a number of different sources can be categorized together.

System F 514 also includes subsystem B 1102 for determining the relevance of data through a perceived relevance for the purpose of a given query or a type of query and then categorizing the data by perceived relevance. Perceived relevance can be provided by a user through the form of a numerical value or a relative value. Perceived relevance can also be provided automatically by the database, hardware, or software according to rules established in the query or query type. Data assigned to a particular perceived relevance level can be categorized together.

System F 514 also includes subsystem C 1104 for determining the relevance of non-current data and categorizing data by whether the data is non-current. Some data become less relevant over time. For example, World War II intelligence data from the year 1943 regarding Nazi German military personnel records is not likely to be relevant to modern intelligence investigations. However, no data is truly useless or obsolete in the database and methods described herein. Thus, such data is stored. To account for the fact that the data is old, the data is assigned less relevance via the use of metadata.

Less relevant data may become relevant under certain circumstances. The relevance of non-current data can also change. For example, if the World War II intelligence data from above leads to an inference that a still-living suspected Nazi war criminal might be living in a particular country, then the data becomes more pertinent to the intelligence investigation. In this case, the relevance of the non-current data increases.

Additionally, non-current data includes data that has less relevance after a given event. For example, data regarding threats to bomb a sporting event become less relevant after the sporting event takes place without incident. However, such data is not obsolete or useless, even if it is less relevant as being non-current.

Whatever the source or reason for being non-current, data at a given level of being non-current can be categorized together. Thus, for example, non-current data regarding threats against a completed sports event could, theoretically, be categorized together with the World War II intelligence data above, at least according to the degree to which each set of data is non-current.

Figure 12:
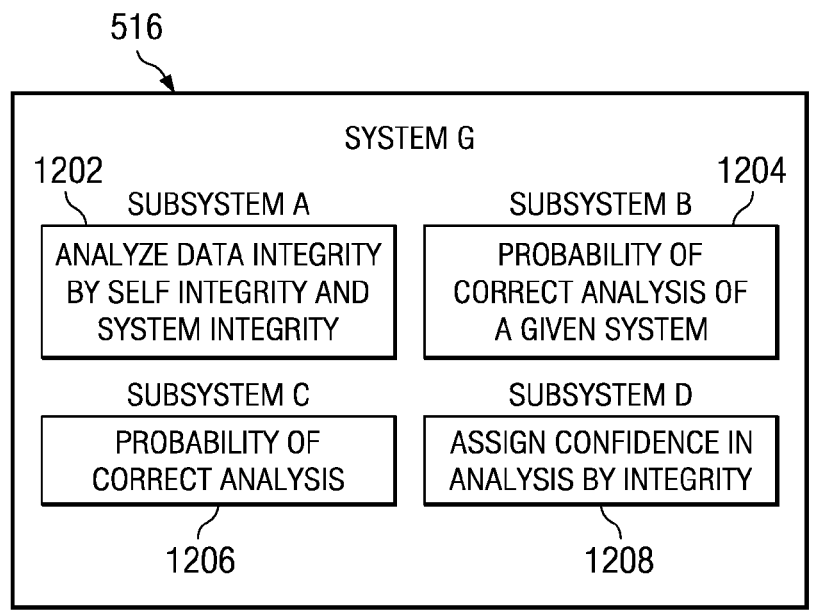
FIG. 12 is a block diagram illustrating functions of a data processing system used with a data processing network and a central database for identifying past, present, or future criminal activity, in accordance with an illustrative embodiment.

FIG. 12 is a block diagram illustrating functions of a data processing system used with a data processing network and a central database for identifying past, present, or future criminal activity, in accordance with an illustrative embodiment. Specifically, FIG. 12 illustrates additional details regarding system G 516 in FIG. 5. System G 516 of FIG. 12 can be implemented via one or more data processing systems connected by a network, as described in FIGS. 1 and 2, or via one or more hardware systems or software programs that can perform the functions of system G 516. System G 516 of FIG. 12 is used in conjunction with other systems and functions of data processing network 500 to allow central database 400 of FIG. 5 to effectively receive and process queries to create probabilities of inferences. System G 516 includes a number of subsystems implemented as one or more hardware or software systems in one or more data processing systems.

System G 516 includes subsystem A 1202 for categorizing data by integrity. System G 516 includes software or hardware for analyzing data integrity by self-integrity and system integrity. Subsystem A 1202 allows the central database to check the degree of self-integrity of received data. Data integrity is the quality of correctness, completeness, wholeness, soundness, and compliance with the intention of the creators of the data. Data integrity is achieved by preventing accidental or deliberate but unauthorized insertion, modification, or destruction of data in a database. Thus, data has a degree of self-integrity according to the degree of the integrity of the data. Data can be categorized according to a given degree of integrity. The degree of integrity can be quantitative, through the use of a numerical scoring system, or qualitative, such as assigning qualitative assessments of data integrity including "low," "medium," and "high."

System G 516 also includes subsystem C 1206 for determining the probability of a correct analysis of a given system based on the integrity of the data. Data having less integrity is less likely to result in an inference with a high probability of correctness.

System G 516 also includes subsystem D 1208 for assigning confidence in an analysis by the integrity of the data. Subsystem D 1208 is different than subsystem B 1204 in that the probability of correct analysis can be estimated according to the data integrity before the actual analysis takes place. This confidence in analysis can also be used when categorizing data by integrity.

Figure 13:
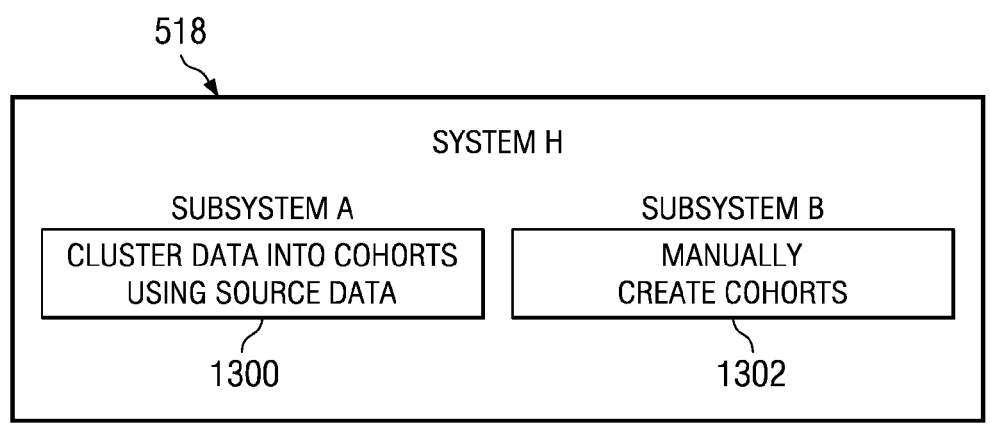
FIG. 13 is a block diagram illustrating functions of a data processing system used with a data processing network and a central database for identifying past, present, or future criminal activity, in accordance with an illustrative embodiment.

FIG. 13 is a block diagram illustrating functions of a data processing system used with a data processing network and a central database for identifying past, present, or future criminal activity, in accordance with an illustrative embodiment. Specifically, FIG. 13 illustrates additional details regarding system H 518 in FIG. 5. System H 518 of FIG. 13 can be implemented via one or more data processing systems connected by a network, as described in FIGS. 1 and 2, or via one or more hardware systems or software programs that can perform the functions of system H 518. System H 518 of FIG. 13 is used in conjunction with other systems and functions of data processing network 500 to allow central database 400 of FIG. 5 to effectively receive and process queries to create probabilities of inferences. System H 518 includes a number of subsystems implemented as one or more hardware or software systems in one or more data processing systems.

FIG. 13 includes software or hardware for creating cohorts. A cohort is a group of associated individuals or objects. A cohort can be treated as a single entity when performing analysis. For example, a cohort can be "all individuals who have received flight instruction." This set of individuals, or cohort, is treated as a single data point during analysis. If more detail is desired, than specific individuals in the cohort or sub-cohorts can be identified and/or searched. A sub-cohort is a cohort; however, a sub-cohort can be said to exist within the domain of a larger cohort. In this example, a sub-cohort could be "all individuals who have a commercial flying license."

System H 518 includes subsystem A 1300 for clustering data into cohorts using source data. Through subsystem A 1300 the database can automatically generate cohorts and sub-cohorts using data stored at an atomic level. Atomic data is data stored at the finest possible degree of granularity. Thus, this process of generating cohorts is powerful in that cohorts can be generated involving any given individual type of data. For example, individuals need not be associated into a cohort in order to associate phone numbers into a cohort. A group of phone numbers can be generated into a cohort according to any parameter, such as, for example, area code. A group of individuals can be in one cohort, a group of phone numbers in a set of area codes can be in another cohort, and a group of individuals having commercial flying licenses can be in a third cohort. A fourth cohort can be automatically generated that represents all individuals in the first cohort having commercial flying licenses and having phone numbers in a particular area code.

System H 518 also includes subsystem B 1302 for receiving manually created cohorts. Subsystem B 1302 allows one or more users to manually create a cohort. A cohort can be manually created by inputting a command to the central database or other software or hardware. The command can be to associate one set of data with another set of data. For example, a user can input a command to associate "people" with "commercial flying licenses" to create a cohort of "people with commercial flying licenses." Central database 400 in FIG. 4 allows this command to be executed successfully.

The cohorts themselves, however, are generated and stored as data in the database. Thus, each generated cohort becomes a new datum for use in central database 400 in FIG. 4.

Figure 14:
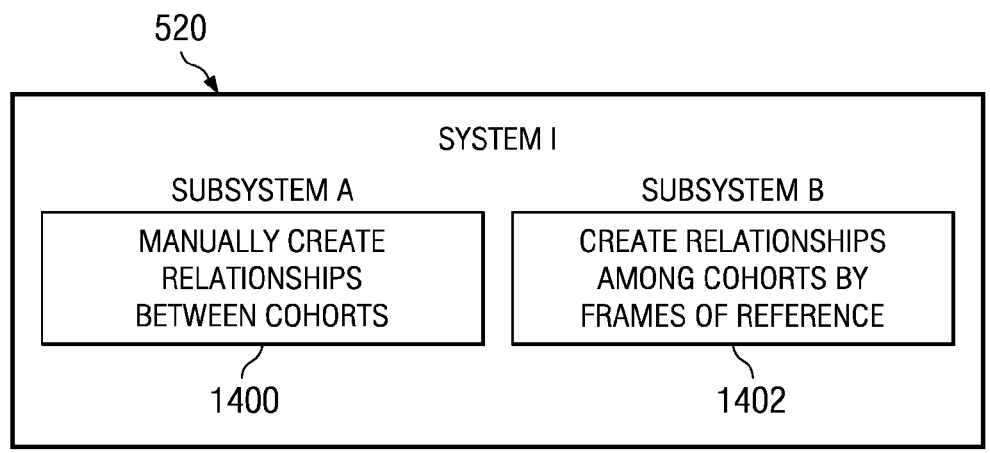
FIG. 14 is a block diagram illustrating functions of a data processing system used with a data processing network and a central database for identifying past, present, or future criminal activity, in accordance with an illustrative embodiment.

FIG. 14 is a block diagram illustrating functions of a data processing system used with a data processing network and a central database for identifying past, present, or future criminal activity, in accordance with an illustrative embodiment. Specifically, FIG. 14 illustrates additional details regarding system 1520 in FIG. 5. System 1520 of FIG. 14 can be implemented via one or more data processing systems connected by a network, as described in FIGS. 1 and 2, or via one or more hardware systems or software programs that can perform the functions of system 1520. System 1520 of FIG. 14 is used in conjunction with other systems and functions of data processing network 500 to allow central database 400 of FIG. 5 to effectively receive and process queries to create probabilities of inferences. System 1520 includes a number of subsystems implemented as one or more hardware or software systems in one or more data processing systems.

System 1520 includes hardware or software for creating relationships among cohorts. Relationships among cohorts can be any relationship. An example of a relationship between cohorts is the association of a first cohort as a sub-cohort of a second cohort. Cohorts can be associated with each other according to mathematical set theory. Cohorts can also be associated with each other according to user-defined associations, such as, for example, associating two cohorts as being weakly or strongly associated with each other.

System 1520 includes subsystem A 1400 for manually creating relationships between cohorts. Thus, users can use hardware or software to create relationships between cohorts for use by central database 400 in FIG. 4. Additionally, system 1520 includes subsystem B 1402 for crating relationships among cohorts by frames of reference. Relationships among cohorts can be associated according a frame of reference in that a frame of reference serves as an anchor for generating associations among cohorts.

For example, a frame of reference can be a fact that a known terrorist has just obtained a commercial flying license. Subsystem B 1402 can generate relationships among existing or new cohorts using this frame of reference. For example, a first cohort is "all individuals with commercial flying licenses." A second cohort is "all known individuals known to associate with the known terrorist." A relationship between these two cohorts can be generated. The relationship between these two cohorts is created by the frame of reference that a known terrorist has obtained a commercial flying license.

Figure 15:
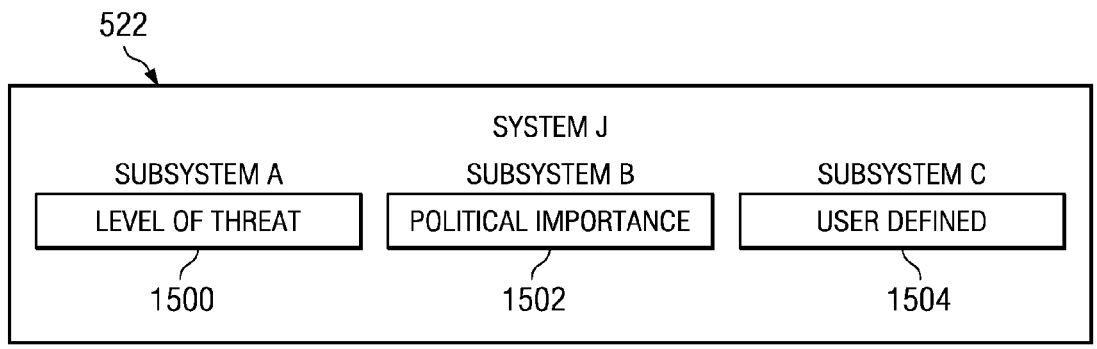
FIG. 15 is a block diagram illustrating functions of a data processing system used with a data processing network and a central database for identifying past, present, or future criminal activity, in accordance with an illustrative embodiment.

FIG. 15 is a block diagram illustrating functions of a data processing system used with a data processing network and a central database for identifying past, present, or future criminal activity, in accordance with an illustrative embodiment. Specifically, FIG. 15 illustrates additional details regarding system J 522 in FIG. 5. System J 522 of FIG. 15 can be implemented via one or more data processing systems connected by a network, as described in FIGS. 1 and 2, or via one or more hardware systems or software programs that can perform the functions of system J 522. System J 522 of FIG. 15 is used in conjunction with other systems and functions of data processing network 500 to allow central database 400 of FIG. 5 to effectively receive and process queries to create probabilities of inferences. System J 522 includes a number of subsystems implemented as one or more hardware or software systems in one or more data processing systems.

System J 522 includes hardware or software for categorizing data by importance. The importance of a given datum is determined qualitatively by a user, but can be assigned a quantitative or qualitative value by the user for use by central database 400 in FIG. 4. System J 522 includes subsystem A 1500 for determining the level of a threat. The level of a threat reflects the seriousness of a threat or crime, as determined by a user. For example, detonation of a nuclear bomb is considered a very serious threat. Note that the reliability of a tip that a nuclear bomb is going to be detonated in a city is factored into system F 514 in FIG. 5, in which data is categorized by relevance. If a person under the influence of hallucinogenic drugs provides the nuclear detonation tip and that individual has no reason to have information regarding nuclear weapons, then the information has a low degree of reliability and thus a low degree of relevance. These two factors, level of threat and relevance (reliability) are taken into account when calculating the probability of an inference.

Once the importance of a datum is determined, system J 522 allows data to be categorized by importance. Thus, data having a particular degree of importance can be grouped together.

System J 522 also includes subsystem B 1502 for calculating or receiving input regarding political importance of a particular datum. For example, a particular crime might be receiving much public attention. Politically, authorities desire to give the investigation of the crime higher importance. This fact can be factored into account using subsystem B 1502. For example, subsystem B 1502 can raise the relevance of a particular fact regarding a person if that person is somehow connected to the crime as a witness.

System J 522 also includes subsystem C 1504 for creating user-defined importance. Thus, a user can establish an importance of a fact. A user can also establish a range of values of importance within which central database 400 in FIG. 4 can adjust a given importance of that fact. A value of importance can be quantitative, in terms of a number value assigned to importance, or qualitative in terms of relative values.

Figure 16:
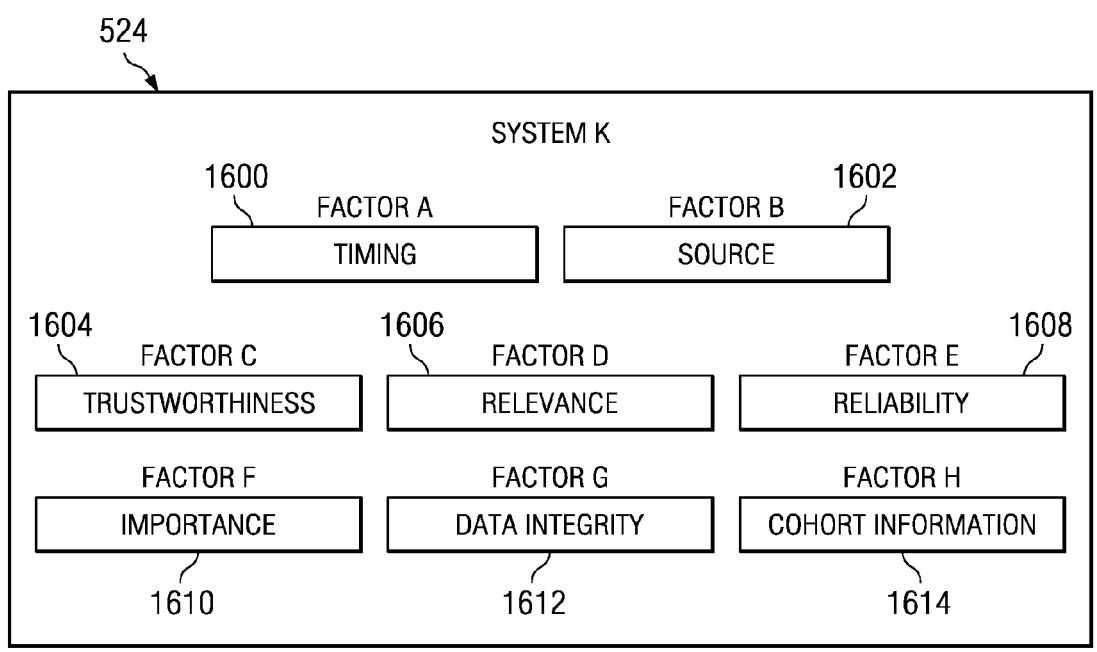
FIG. 16 is a block diagram illustrating functions of a data processing system used with a data processing network and a central database for identifying past, present, or future criminal activity, in accordance with an illustrative embodiment.

FIG. 16 is a block diagram illustrating functions of a data processing system used with a data processing network and a central database for identifying past, present, or future criminal activity, in accordance with an illustrative embodiment. Specifically, FIG. 16 illustrates additional details regarding system K 524 in FIG. 5. System K 524 of FIG. 16 can be implemented via one or more data processing systems connected by a network, as described in FIGS. 1 and 2, or via one or more hardware systems or software programs that can perform the functions of system K 524. System K 524 of FIG. 16 is used in conjunction with other systems and functions of data processing network 500 to allow central database 400 of FIG. 5 to effectively receive and process queries to create probabilities of inferences. System K 524 includes a number of factors determined by one or more hardware or software systems in one or more data processing systems.

System K 524 assigns probabilities to inferences. An inference might be drawn based on comparing data in the database, but the inference might be strong or weak. The strength of an inference is described in terms of a probability. The probability reflects the relative percentage chance that the inference is true.

Many factors influence the probability of one or more inferences. Examples of factors include factor A 1600, timing; factor B 1602, source; factor C 1604, trustworthiness; factor D 1606, relevance; factor E 1608, reliability; factor F 1610, importance; factor G 1612, data integrity; and factor H 1614, cohort information. Many of these factors are determined using other systems, such as system A 504 through system J 522.

Factor A 1600, timing, can influence the probability that an inference is true in that the temporal relationship between facts can have a significant impact on the likelihood of a correct inference. For example, referring to the example of World War II Nazi German intelligence above, the fact that the intelligence is very old can decrease the probability that an inference drawn based on that information is true. In contrast, information that a known bomber purchased excessive or illegal explosives one day before a major terrorist event would increase the probability of an inference that the known bomber perpetrated the terrorist event.

Factor B 1602, source, can also influence the probability that an inference is true. If the source of information is a known drug addict convicted of multiple counts of felony perjury, then a decrease results in the probability that an inference drawn from information from the known drug addict is true. Similarly, information garnered from a random Internet Web site is probably less likely to be true, though information gathered from a known expert in a field is more likely to be true. Thus, the source of the information influences the probability that an inference is true or false.

Factor C 1604, trustworthiness also influences the probability that an inference is true. Trustworthiness can be related to source, timing, reliability, and other factors. However, a user or the hardware or software can assign an independent separate trustworthiness score, either quantitative or qualitative, to a set of data. Thus, for example, a user or the hardware or software could increase the probability that the known drug user is providing trustworthy information based on previous specific information from that known drug user or based on corroborative evidence.

Factor D 1606, relevance, can also influence the probability that an inference is true. Information that a country in Africa recently declared war on a country in Asia probably has little relevance to whether or not a domestic terrorist in the United States is plotting to bomb a domestic target in the United States. That information might still be considered, though the probability that the two facts are related is small given that they do not seem relevant to each other. Thus, probability of an inference that a domestic terrorist is plotting a domestic bombing is relatively low in view of the fact of the declaration of war. In turn, the probability of such an inference increases in view of a different fact with higher relevance, such as, for example, if the domestic terrorist is discovered to be associating with a close group of other known bombers.

Factor E 1608, reliability, can also influence the probability that an inference is true. Reliability of data can be influenced by a number of the other factors described in relation to system K 524. Like factor C 1604, trustworthiness, however, a user or hardware or software can assign an independent reliability score, quantitative or qualitative, that indicates the reliability of data.

Factor F 1610, importance, can also influence the probability that an inference is presented to a user. Although the importance of a fact does not necessarily translate to the correctness of the fact, the importance of the fact can influence whether a user is presented with the probability of truth of an inference drawn based on that fact.

Thus, for example, the known drug user described above provides information relating to a plot to assassinate a political figure. This plot is considered important. Although the source is considered unreliable, thereby reducing the probability of an inference that the plot is true, the fact that the plot is considered important increases the probability that the inference will be presented to the user.

Additionally, factor G 1612, data integrity, can influence the probability that an inference is true. Data that is considered to have good integrity is more likely to be correct, reliable, and trustworthy. Hence, data with good integrity can increase the probability that an inference drawn on that data is true. In contrast, data that does not have good integrity has the opposite effect—to decrease the probability that an inference drawn on that data is true.

Additionally, factor H 1614, cohort information, can influence the probability that an inference is true. For example, the domestic terrorist described above is associated with a cohort that is made up of known bombers. The fact that the known bomber can be associated in recent time with the cohort increases the probability of truth of the inference that the domestic terrorist is engaged in terrorist activity.

Additionally, each of the factors 1602 through 1614 can have synergistic effects on the total probability that an inference is true. Thus, the probabilities are not necessarily linearly additive. Considered as a whole, several facts considered together could synergistically increase or decrease the total probability that an inference is true. In other words, in terms of assigning probabilities to inferences, the whole of all information is greater than the sum of the bits of information that make up the whole. Furthermore, each of the factors 1602 through 1614 can be modified by a user or hardware or software via independent scores associated with a corresponding factor.

Figure 17:
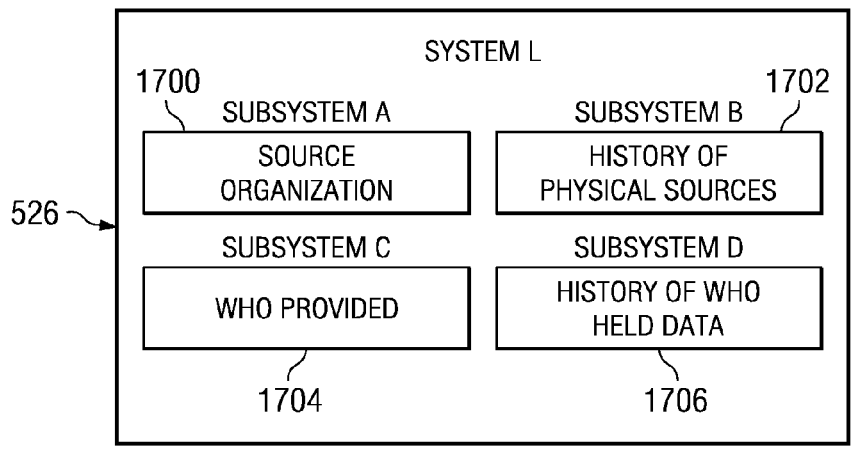
FIG. 17 is a block diagram illustrating functions of a data processing system used with a data processing network and a central database for identifying past, present, or future criminal activity, in accordance with an illustrative embodiment.

FIG. 17 is a block diagram illustrating functions of a data processing system used with a data processing network and a central database for identifying past, present, or future criminal activity, in accordance with an illustrative embodiment. Specifically, FIG. 17 illustrates additional details regarding system L 526 in FIG. 5. System L 526 of FIG. 17 can be implemented via one or more data processing systems connected by a network, as described in FIGS. 1 and 2, or via one or more hardware systems or software programs that can perform the functions of system L 526. System L 526 of FIG. 17 is used in conjunction with other systems and functions of data processing network 500 to allow central database 400 of FIG. 5 to effectively receive and process queries to create probabilities of inferences. System L 526 includes a number of subsystems implemented as one or more hardware or software systems in one or more data processing systems.

System L 526 categorizes data by source. As described above, the source of data can influence the probability of truth of an inference drawn from that data. Additionally, the category of data can, itself, be used to draw inferences.

Thus, system L 526 includes subsystem A 1700 for organizing data according to source organization. A source organization is the organization that derived the data or from which the data was received. Examples of source organizations include federal and state agencies, corporations, religious institutions, and others. System L 526 also includes subsystem B 1702 for organizing data by history of physical sources. A history of physical sources is a chain of computers on which data was stored. For example, if data was generated on computers A through G, transferred to computers H through W, and finally transferred to computers X through Z, then the history of physical sources would include all of computers A through Z in the provided order at the provided times.

System L 526 includes subsystem C 1704 for organizing data according to who provided the data. Thus, the source of data can be categorized not only by organization but also by individual, cohorts of individuals, and cohorts of organizations.

System L 526 also includes subsystem D 1706 for organizing data according to a history of who held data. A history of who held data is similar to a chain of custody in that the history of who held data is a listing of the order in which individuals, organizations, or cohorts held particular data at particular times.

FIG. 18 is a block diagram of illustrating components and operating characteristics of a central database for identifying past, present, or future criminal activity, in accordance with an illustrative embodiment. Central database 400 of FIG. 18 is central database 400 of FIG. 5. Central database 400 can be implemented via one or more data processing systems connected by a network, as described in FIGS. 1 and 2, or via one or more hardware systems or software programs that can perform the functions of central database 400. Central database 400 of FIG. 18 is used in conjunction with other systems and functions of data processing network 500 to allow central database 400 to effectively receive and process queries to create probabilities of inferences.

FIG. 6 through FIG. 17 describe characteristics of data processing network 500 in terms of what data processing network 500 does. FIG. 18 describes, together with FIGS. 20A and 20B, what central database 400 is.

In particular, central database 400 has a number of characteristics. Characteristic A 1800 is that all data is tagged with time stamps. This property means that each datum is associated with metadata that reflects a time stamp as to when the datum was received in the database. A time stamp can also include additional times, such as when a datum was created, when a datum was modified, and when a datum was accessed. Additional data can be used to indicate when a datum was deleted.

Characteristic B 1802 is that data is stored at an atomic level. Data stored at an atomic level is data stored at the finest possible degree of granularity. Thus, for example, data regarding a person is not necessarily stored under a person's name. Instead, data regarding the person is stored separately as name, address, phone number, and other information regarding the person. Each fact is stored as an individual datum. Metadata allow central database 400 to create a profile of the person associated with the name.

Characteristic C 1804 is that the levels of granularity of the data are conformed to the dimensions of the database. Not all data is stored at the finest degree of granularity. The degree of granularity is the degree to which data can be stored at an atomic level. While data is stored at the finest degree of granularity possible, some data must be stored at higher degrees of granularity because of how the data was generated or discovered. However, no matter what the degree of granularity of data, all data is conformed to the dimensions of the database.

The term "data is conformed to the dimensions of the database" means that, for the entire database, any dimension will have the same meaning to all data elements that use the dimension as a reference. Specifically, data is conformed to the dimensions of the database when two dimensions share the same foreign key. A foreign key is an object that links data to a dimension. Thus, all data elements that share the same foreign key have the same frame of reference.

Characteristic D 1806 is that hierarchy is determined by the dimensionality of the database. As described above, all data conform to the dimensions of the database. In this way, a hierarchy of data can be established for each characteristic of a datum.

For example, because the data conform to the dimensions of the database, all data elements that reference a location dimension will "perceive" the location in the same way. The same location could be shared by different events and people. By conforming the data to the dimensions of the database, a query can be made to ask what other events are associated with the particular location. Additionally, a query can be made to ask what other events are associated with other locations within a hierarchy of locations. For example, an event may occur at a home address, and the hierarchy of locations could be a block, a city, a commercial zone, a county, a congressional district, a state, a country, or any other means for denoting locations within a hierarchy associated with a particular location.

Characteristic E 1808 is that data is tagged by the source of the data. Thus, for example, each datum in the database has associated with it metadata that tags the datum by the source of the data. In this way, the identity, and possibly other characteristics such as location, and contact information of the source of each datum is known and can be queried.

Characteristic F 1810 is that data is tagged by channel. A channel is the method by which data is obtained. For example, if data is downloaded via the Internet, then the channel is the Internet network and the source is the host data processing system. If data is received in the form of pictures delivered by courier, then the channel is hand delivery by the courier. In any case, data regarding the channel is tagged as metadata associated with the corresponding datum.

Characteristic G 1812 is that data is tagged by location. This characteristic means that each datum is associated with metadata that includes information regarding the location of where the data is stored. Central database 400 can be extremely large, tens of thousands of terabytes and possibly vastly more, and spread across numerous data processing systems and storage devices. To facilitate the location of data, each datum is associated with metadata that indicates the location of the data.

Characteristic H 1814 is that all cohorts are maintained in central database 400. Cohorts are groups of objects or people that share common characteristics or are otherwise part of a group. Each cohort is, itself, stored as data in central database 400. Thus, once a cohort is generated, that cohort remains permanently in central database 400 for further reference and comparison.

Characteristic I 1816 is that events are modeled as inverted star schemas. A star schema (sometimes referenced as star join schema) is the simplest data warehouse schema, including a single fact table with a compound primary key, with one segment for each dimension and with additional columns of additive, numeric facts. The star schema makes multi-dimensional database (MDDB) functionality possible using a traditional relational database. Fact tables in star schema are mostly in third normal form (3NF), but dimensional tables are in de-normalized second normal form (2NF). Normalized dimensional tables look like snowflakes.

In an inverted star schema, a star schema or a constellation of star schemas can be viewed from any point. Thus, a command can be issued to a database to refold and refocus the database, mathematically speaking, with respect to a particular point in the star schema. No true physical transformation of the database need occur.

In an illustrative example, a star schema database relates a business transaction with a sale in the center, a merchant connected to the sale on the right side and a buyer connected to the sale on the left side. In an inverted star schema, the database is refolded and refocused such that the merchant is the center of the star schema. Similarly, the buyer could be made the center of the star schema.

FIG. 19 is a block diagram illustrating subsystems for selection and processing of data using a central database for identifying past, present, or future criminal activity, in accordance with an illustrative embodiment. Each subsystem shown in FIG. 19 can be implemented using one or more hardware or software components in one or more data processing systems. In some embodiments, more than one subsystem can be implemented using the same hardware or software. Each subsystem shown in FIG. 19 describes a function or action that occurs during selection and processing in system M 502 of FIG. 5.

Subsystem A 1900 crawls text. The term "crawl text" means that text is searched for words, characters, or strings of information. Optionally, during text crawling, text is parsed into words, characters, or strings and stored for future use. During selection and processing text related to or retrieved for a query that has not already been crawled can be crawled. Additionally, text entered as part of a query can be crawled.

Subsystem B 1902 generates and stores summaries of a query, results of a query, or intermediate results of a query. Summaries can be presented to a user in various different form, such as text, charts, graphs, images, or voice text, for subsequent analysis. Similarly, subsystem C 1904 stores each query. Thus, every query made to central database 400 becomes part of the data stored in central database 400.

Subsystem D 1906 defines and tags extracted or derived data. Data extracted or derived during selection and processing of queries or data is defined and tagged as part of the query or selection and processing process. Thus, additional metadata can be added to each datum extracted or derived during selection and processing. Similarly, additional data can be created during selection and processing.

Subsystem E 1908 relates events and multiple hierarchies. Subsystem E 1908 uses inverted star schemas to relate a particular event to other related data. For example, an event can be related to a person associated with the event. However, because the dimensions of the data conform to the database and because all data are associated with hierarchies, the person can be associated with groups of people. For example, a particular suspect could be associated with a criminal organization. Thus, subsystem E 1908 allows the database to relate the particular event to the suspect and also to the criminal organization to which the suspect belongs. In other words, events are related to multiple hierarchies.

Subsystem F 1910 analyzes past data to identify current relevance. Non-current data, such as data described subsystem C 1104 of FIG. 11, could possibly be relevant to a current situation; thus, non-current data and past data is analyzed along with current data. Subsystem F 1910 analyzes the past data to identify any current relevance that might exist. Not all non-current data in central database 400 is necessarily analyzed; instead, only non-current data related to the query is analyzed in order to conserve processing overhead.

Subsystem G 1912 receives and updates data annotated by a system analyst, or user. Thus, a user can update data or metadata in central database 400.

Subsystem H 1914 assigns probabilities to inferences and probabilities to the trustworthiness and reliability of data. Subsystem H 1914 compliments, or may be part of system G 516 of FIG. 12 or system K 524 of FIG. 16. However, subsystem H 1914 can operate independently of these systems during selection and processing of queries in order to divide the processing resources used to execute a query and continually update central database 400. However, subsystem H 1914 operates in a manner similar to system G 516 and system K 524.

Subsystem 11916 assigns a category to a probability generated by subsystem H 1914. Probabilities are categorized by fact, inference, trustworthiness, reliability, from which source a fact was derived, and many other categorizations.

Subsystem J 1918 identifies new cohorts. Identification of new cohorts is a valuable part of selection and processing of a query. New cohorts are identified by comparing initially unrelated data, identifying patterns in the initially unrelated data, and then relating that data to create a cohort from that data.

For example, suspect A and suspect B are both known terrorists; however, suspect A is a domestic terrorist who has previously not had a relationship with suspect B who is a foreign terrorist. During selection and processing of a query related to a terrorist activity, system M 502 identifies that suspect A and suspect B were both in a common location within the same day. Subsystem J 1918 creates a new cohort including "suspect A and suspect B" based on the co-location of the suspects closely in time. This new cohort can be used during further selection and processing. This new cohort may be presented to a user. The user may, depending on circumstances, decide that suspect A and suspect B are forming a new terrorist cell. The user, though subsystem G 1912 (annotation), can label the cohort including "suspect A and suspect B" as a possible new terrorist cell. This information is then included in central database 400, whereupon selection and processing continues in order to generate more information regarding possible activities of the possible new terrorist cell.

Subsystem K 1920 produces a summary of results and conclusions for presentation to a user. The summary of results can take any useful form, such as text, charts, graphs, graphics, video, audio, or other forms. The summary of results can also be modified for presentation to particular users. For example, text can be adapted to use different languages or terms of greatest usefulness to a given user.

Subsystem L 1922 identifies specific relationships from new cohorts. Using the example of suspect A and suspect B above, subsystem J 1918 identified those two individuals as a new cohort. A new relationship between suspect A and suspect B as superior and underling might be identified. Additionally, a relationship between suspect A and previously unrelated suspect C might be established simply because suspect A and suspect B have been incorporated into a new cohort.

Figure 22:
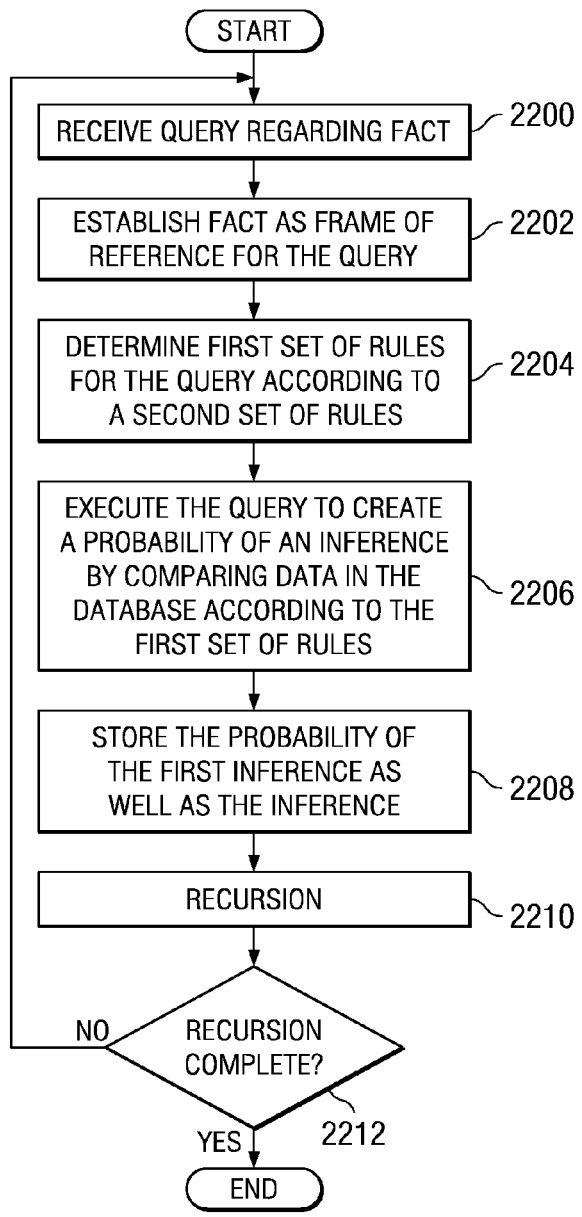
FIG. 22 is a flowchart illustrating execution of a query in a database to establish a probability of an inference based on data contained in the database, in accordance with an illustrative embodiment.
Figure 23A:
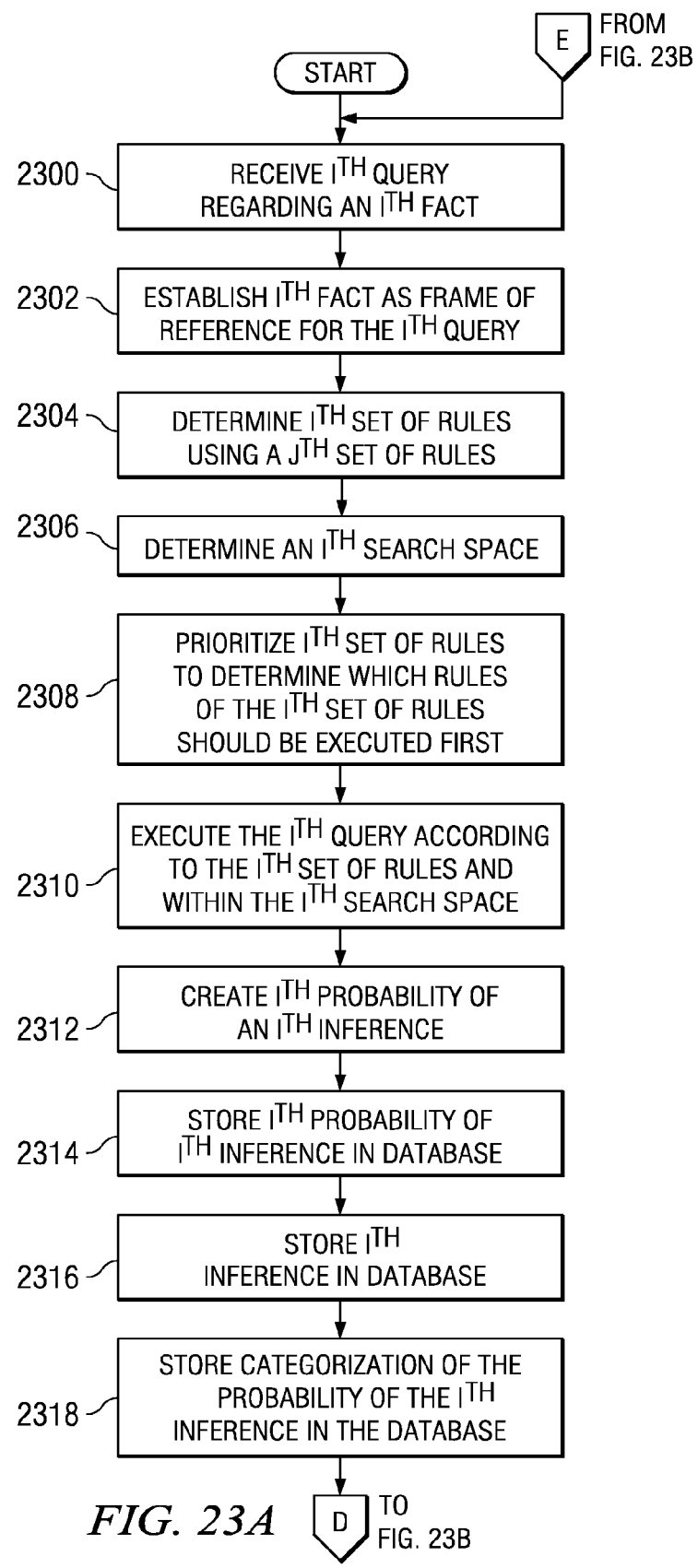
FIGS. 23A and 23B are a flowchart illustrating execution of a query in a database to establish a probability of an inference based on data contained in the database, in accordance with an illustrative embodiment.
Figure 23B:
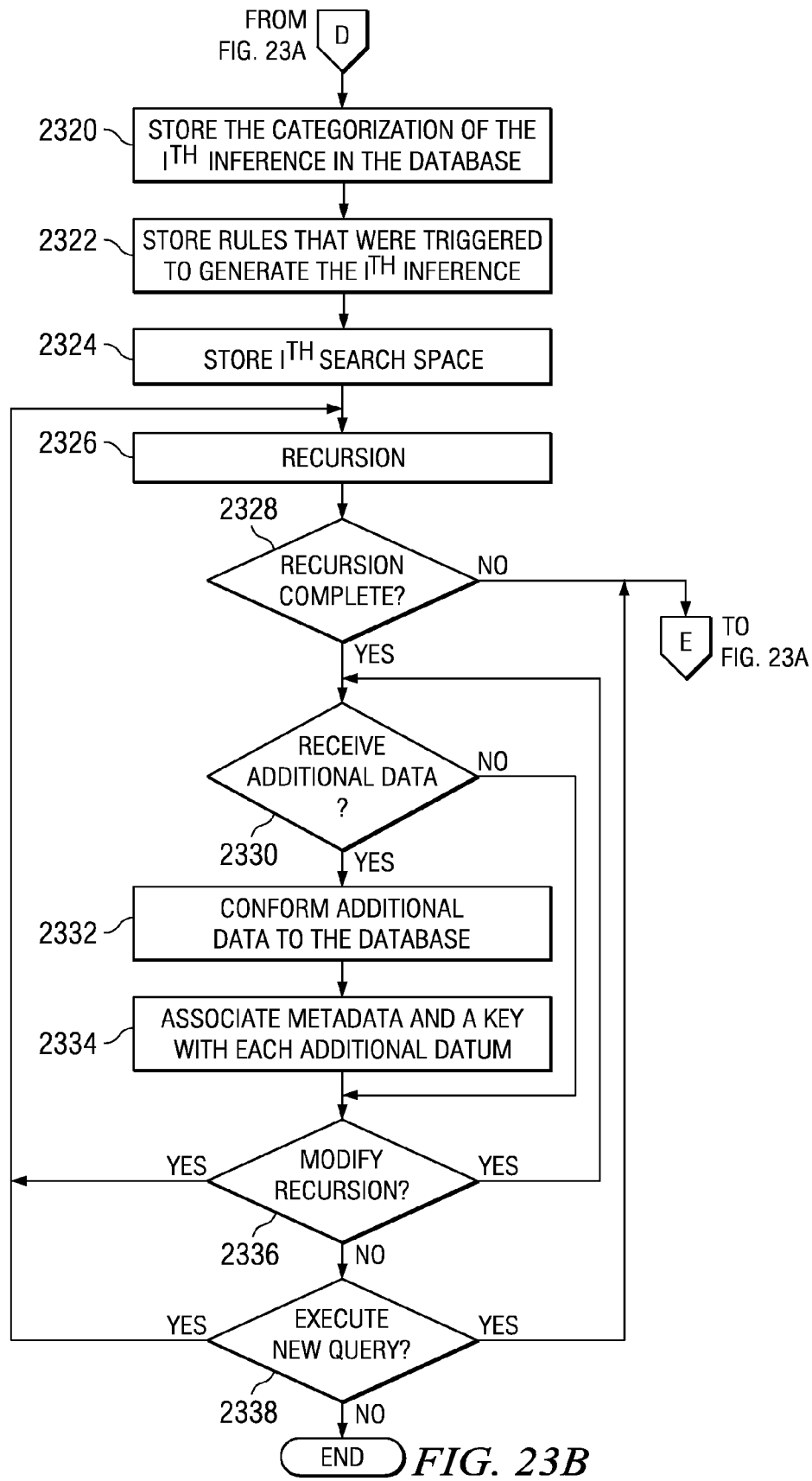

Subsystem M 1924 provides nearly continual recursion of queries. The entire process of analysis, as shown in FIG. 22 and FIGS. 23A and 23B, is performed over and over again. During each iteration each new inference and each new probability of an inference is included in central database 400. The addition of this new information can change the results of the inference and the probability of the inference, and can also generate new inferences of interest.

The process of recursion proceeds until a threshold is met. In one example, a threshold is a probability of an inference. When the probability of an inference decreases below a particular number, the recursion is made to stop. In another example, a threshold is a number of recursions. Once the given number of recursions is met, the process of recursion stops. Other thresholds can also be used.

Figure 20A:
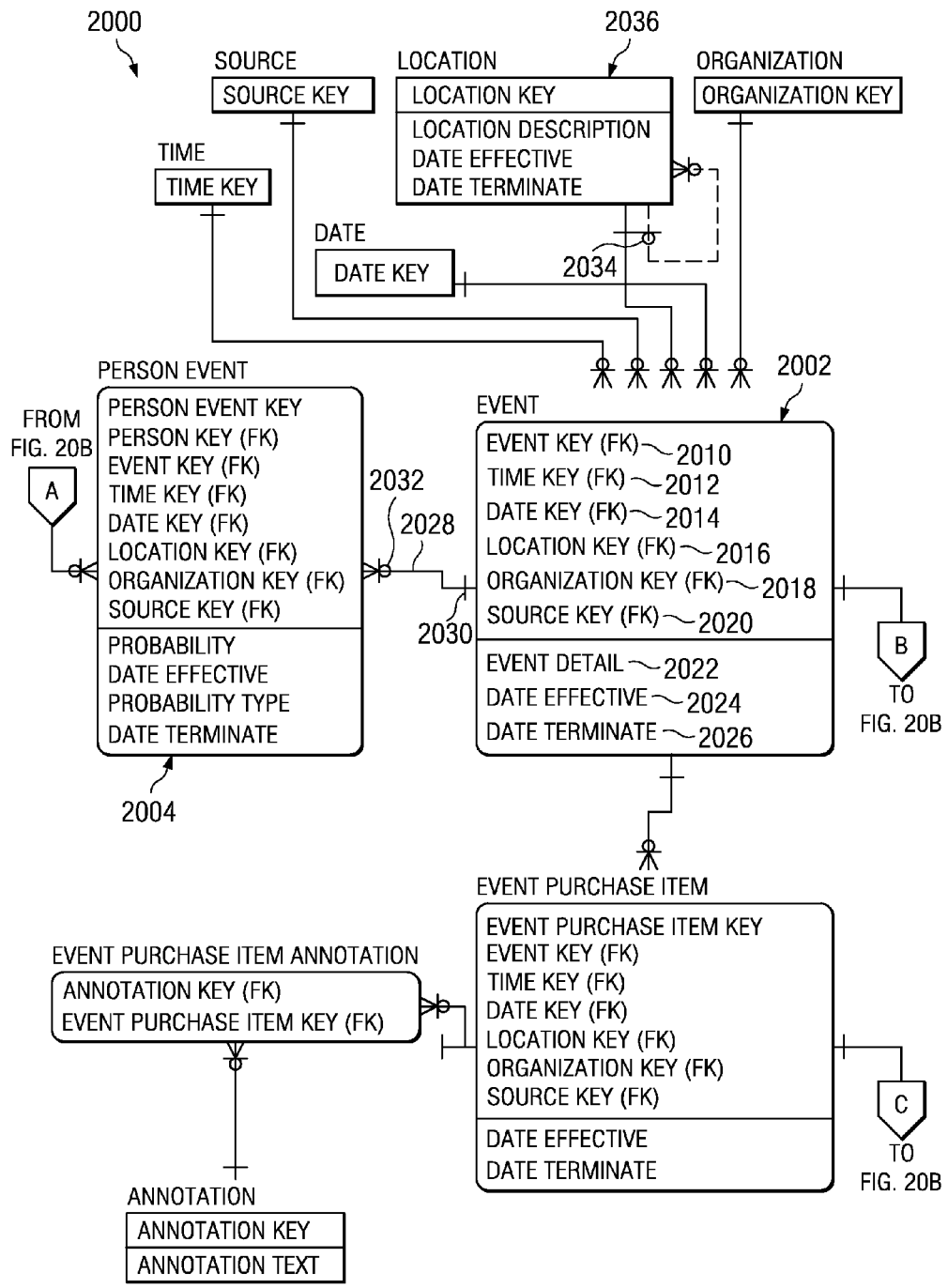
FIGS. 20A and 20B are an exemplary structure of a database that can be used for a central database, in accordance with an illustrative embodiment.
Figure 20B:
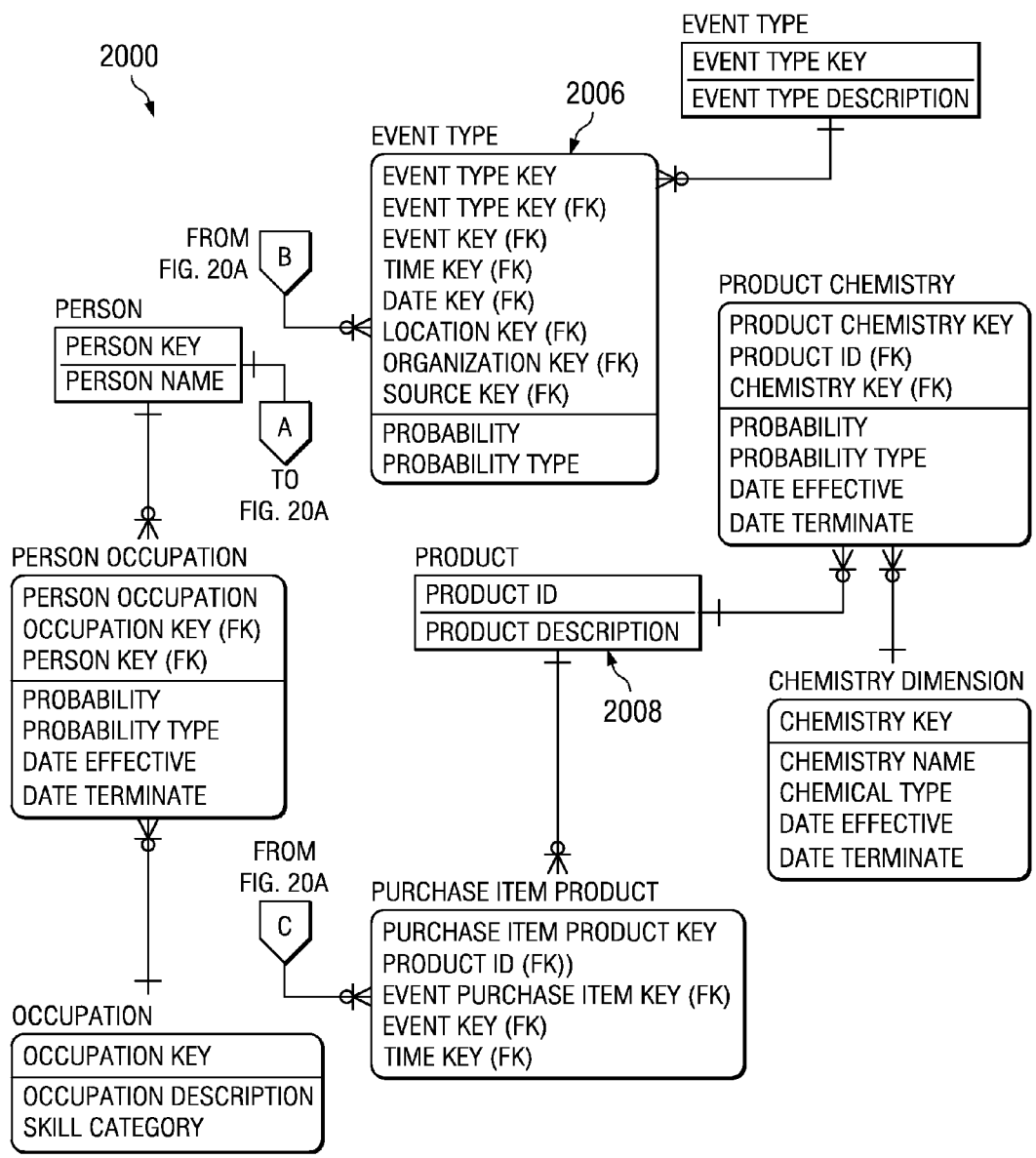

FIGS. 20A and 20B are an exemplary structure of a database that can be used for central database 400. FIGS. 20A and 20B show entity relation data model 2000. Entity relation data model 2000 can be created using standardized notation for generating representations of database structures for large and/or complex databases. Entity relation data model 2000 can be implemented as one or more databases and/or applications in one or more data processing systems which can be connected over a network. For example, entity relation data model 2000 can be implemented using servers 104 and 106, clients 110, 112, 114, storage 108, and network 102 shown in FIG. 1.

In entity relation data model 2000 shown in FIGS. 20A and 20B, event 2002 is in the center of an inverted star schema. An inverted star schema is described with respect to subsystem E 1908 in FIG. 19. Thus, other entities, such as person event 2004, event type 2006, product 2008, or any other entity can be made the center of entity relation data model 2000. A entity is a box having a name or title outside the box, wherein a box may have a dividing line. Event 2002 contains a number of keys, including event key 2010 that uniquely identifies the event. Event 2002 contains foreign keys associated with event 2002, including time key 2012, date key 2014, location key 2016, organization key 2018, and source key 2020. Thus, event 2002 can be related to time, date, location of the event, organizations involved with the event, and the source of where such data comes from. Other foreign keys can be associated with event 2002, possibly numerous additional foreign keys. Event 2002 also contains details, such as event 2022, the effective date of the event 2024, the date on which the event terminated 2026, and possibly other details.

Other entities, such as entities 2004, 2006, 2008, and the other entities shown in FIGS. 20A and 20B also contain similar structures. Structures include keys, foreign keys, and details or notes regarding the event.

Entities are related to each other using the lines shown. A solid line indicates a relationship between objects. Thus, for example, line 2028 indicates a relationship between person event 2004 and event 2002. Symbol 2030 indicates the "one side" of a one to many relationship. Symbol 2032 indicates the "many side" of one to many relationship. Thus, for example, event 2002 relates to many different people, including person event 2004, as shown in FIGS. 20A and 20B. Other similar relationships are shown between the various entities shown in FIGS. 20A and 20B. Other symbols can be used. For example, symbol 2034 indicates a many to one recursive relationship among locations in location entity 2036.

The illustrative entity relation model shown in FIGS. 20A and 20B is exemplary. More or fewer entities can appear in an entity relation model used in different aspects of the methods and devices described herein. In an illustrative embodiment, a vast number of entities can exist, each having vast numbers of keys, foreign keys, and associated details.

Figure 21:
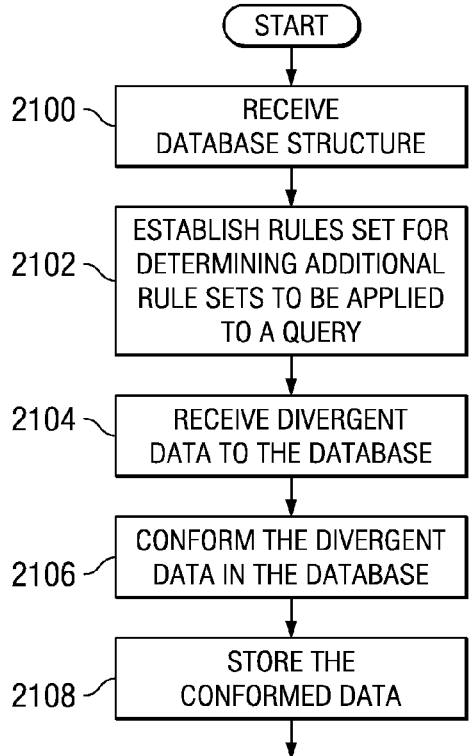
FIG. 21 is a flowchart illustrating establishment of a database adapted to establish a probability of an inference based on data contained in the database, in accordance with an illustrative embodiment.

FIG. 21 is a flowchart illustrating establishment of a database adapted to establish a probability of an inference based on data contained in the database, in accordance with an illustrative embodiment. The process shown in FIG. 21 can be implemented using central database 400, data processing network 500, and system M 502, all of FIG. 5. In an illustrative embodiment, each of central database 400, data processing network 500, and system M 502 can be implemented in a single data processing system or across multiple data processing systems connected by one or more networks. Whether implemented in a single data processing system or across multiple data processing systems, taken together all data processing systems, hardware, software, and networks are together referred-to as a system. The system implements the process.

The process begins as the system receives the database structure (step 2100). The database can have a structure similar to that shown in FIGS. 20A and 20B, though the database structure can vary and is likely to be much more complex than the structure shown in FIGS. 20A and 20B. However, the fundamental nature of the structure is similar to that presented in FIGS. 20A and 20B.

Next, the system establishes a rules set for determining additional rule sets to be applied to a query (step 2102). Processing resources are limited. Central database 400 can be extremely large and the number of possible interactions and relationships among all data in central database 400 can be exponentially much larger still. Thus, rules are established in order to limit the scope of comparison. In an illustrative example, the query or facts related to the query are used to establish a frame of reference for the query. The frame of reference is used to limit the scope of the query so that not all data in central database 400 need be searched and not all interactions among the searched data need be analyzed. However, the process of establishing those search rules should preferably be performed by the system because the system has all of the information useful for determining the scope of the search, the search space, and other factors for limiting the query. Additionally, not all users will be familiar enough with central database 400, the system, or computer programming to create a useful set of search rules. Therefore, the system establishes a set of determination rules used to determine the search rules used during a query (step 2102).

The system also receives divergent data in central database 400 (step 2104). Divergent data is sets of data having different types, sizes, compatibilities, and other differences. Divergent data can be received from many different sources.

The system conforms received divergent data to the database (step 2106). As described with respect to FIG. 19 and FIGS. 20A and 20B, data is conformed to the dimensions of the database when two dimensions share the same foreign key. The system then stores conformed data as part of central database 400 (step 2108). The process terminates thereafter.

FIG. 22 is a flowchart illustrating execution of a query in a database to establish a probability of an inference based on data contained in the database, in accordance with an illustrative embodiment. The process shown in FIG. 22 can be implemented using central database 400, data processing network 500, and system M 502, all of FIG. 5. In an illustrative embodiment, each of central database 400, data processing network 500, and system M 502 can be implemented in a single data processing system or across multiple data processing systems connected by one or more networks. Whether implemented in a single data processing system or across multiple data processing systems, taken together all data processing systems, hardware, software, and networks are together referred-to as a system. The system implements the process.

The process begins as the system receives a query regarding a fact (step 2200). The system establishes the fact as a frame of reference for the query (step 2202). The system then determines a first set of rules for the query according to a second set of rules (step 2204). The system executes the query according to the first set of rules to create a probability of an inference by comparing data in the database (step 2206). The system then stores the probability of the first inference and also stores the inference (step 2208).

The system then performs a recursion process (step 2210). During the recursion process steps 2200 through 2208 are repeated again and again, as each new inference and each new probability becomes a new fact that can be used to generate a new probability and a new inference. Additionally, new facts can be received in central database 400 during this process, and those new facts also influence the resulting process. Each conclusion or inference generated during the recursion process can be presented to a user, or only the final conclusion or inference made after step 2212 can be presented to a user, or a number of conclusions made prior to step 2212 can be presented to a user.

The system then determines whether the recursion process is complete (step 2212). If recursion is not complete, the process between steps 2200 and 2210 continues. If recursion is complete, the process terminates.

FIGS. 23A and 23B are a flowchart illustrating execution of a query in a database to establish a probability of an inference based on data contained in the database, in accordance with an illustrative embodiment. The process shown in FIGS. 23A and 23B can be implemented using central database 400, data processing network 500, and system M 502, all of FIG. 5. In an illustrative embodiment, each of central database 400, data processing network 500, and system M 502 can be implemented in a single data processing system or across multiple data processing systems connected by one or more networks. Whether implemented in a single data processing system or across multiple data processing systems, taken together all data processing systems, hardware, software, and networks are together referred to as a system. The system implements the process.

The process begins as the system receives an Ith query regarding an $I^{th}$ fact (step 2300). The term "$I^{th}$" refers to an integer, beginning with one. The integer reflects how many times a recursion process, referred to below, has been conducted. Thus, for example, when a query is first submitted that query is the $1^{st}$ query. The first recursion is the $2^{nd}$ query. The second recursion is the $3^{rd}$ query, and so forth until recursion I-1 forms the "$I^{th}$" query. Similarly, but not the same, the $I^{th}$ fact is the fact associated with the $I^{th}$ query. Thus, the $1^{st}$ fact is associated with the $1^{st}$ query, the $2^{nd}$ fact is associated with the $2^{nd}$ query, etc. The $I^{th}$ fact can be the same as previous facts, such as the $I^{th}$-1 fact, the $I^{th}$-2 fact, etc. The $I^{th}$ fact can be a compound fact. A compound fact is a fact that includes multiple sub-facts. The $I^{th}$ fact can start as a single fact and become a compound fact on subsequent recursions or iterations. The $I^{th}$ fact is likely to become a compound fact during recursion, as additional information is added to the central database during each recursion.

After receiving the $I^{th}$ query, the system establishes the $I^{th}$ fact as a frame of reference for the Ith query (step 2302). A frame of reference is an anchor datum or set of data that is used to limit which data are searched in central database 400, that is defines the search space. The frame of reference also is used to determine to what rules the searched data will be subject. Thus, when the query is executed, sufficient processing power will be available to make inferences.

The system then determines an $I^{th}$ set of rules using a $J^{th}$ set of rules (step 2304). In other words, a different set of rules is used to determine the set of rules that are actually applied to the $I^{th}$ query. The term "$J^{th}$" refers to an integer, starting with one, wherein J=1 is the first iteration of the recursion process and I-1 is the $J^{th}$ iteration of the recursion process. The $J^{th}$ set of rules may or may not change from the previous set, such that $J^{th}$-1 set of rules may or may not be the same as the $J^{th}$ set of rules. The term "$J^{th}$" set of rules refers to the set of rules that establishes the search rules, which are the $I^{th}$ set of rules. The $J^{th}$ set of rules is used to determine the $I^{th}$ set of rules.

The system then determines an $I^{th}$ search space (step 2306). The $I^{th}$ search space is the search space for the $I^{th}$ iteration. A search space is the portion of a database, or a subset of data within a database, that is to be searched.

The system then prioritizes the $I^{th}$ set of rules, determined during step 2304, in order to determine which rules of the $I^{th}$ set of rules should be executed first (step 2308). Additionally, the system can prioritize the remaining rules in the $I^{th}$ set of rules. Again, because computing resources are not infinite, those rules that are most likely to produce useful or interesting results are executed first.

After performing steps 2300 through 2306, the system executes the $I^{th}$ query according to the $I^{th}$ set of rules and within the $I^{th}$ search space (step 2310). As a result, the system creates an $I^{th}$ probability of an Ith inference (step 2312). As described above, the inference is a conclusion based on a comparison of facts within central database 400. The probability of the inference is the likelihood that the inference is true, or alternatively the probability that the inference is false. The Ith probability and the $I^{th}$ inference need not be the same as the previous inference and probability in the recursion process, or one value could change but not the other. For example, as a result of the recursion process the Ith inference might be the same as the previous iteration in the recursion process, but the $I^{th}$ probability could increase or decrease over the previous iteration in the recursion process. In contrast, the $I^{th}$ inference can be completely different than the inference created in the previous iteration of the recursion process, with a probability that is either the same or different than the probability generated in the previous iteration of the recursion process.

Next, the system stores the $I^{th}$ probability of the $I^{th}$ inference as an additional datum in central database 400 (step 2314). Similarly, the system stores the $I^{th}$ inference in central database 400 (step 2316), stores a categorization of the probability of the $I^{th}$ inference in central database 400 (step 2318), stores the categorization of the $I^{th}$ inference in the database (step 2320), stores the rules that were triggered in the $I^{th}$ set of rules to generate the $I^{th}$ inference (step 2322), and stores the Ith search space (step 2324). Additional information generated as a result of executing the query can also be stored at this time. All of the information stored in steps 2314 through 2324, and possibly in additional storage steps for additional information, can change how the system performs, how the system behaves, and can change the result during each iteration.

The process then follows two paths simultaneously. First, the system performs a recursion process (step 2326) in which steps 2300 through 2324 are continually performed, as described above. Second, the system determines whether additional data is received (step 2330).

Additionally, after each recursion, the system determines whether the recursion is complete (step 2328). The process of recursion is complete when a threshold is met. In one example, a threshold is a probability of an inference. When the probability of an inference decreases below a particular number, the recursion is complete and is made to stop. In another example, a threshold is a number of recursions. Once the given number of recursions is met, the process of recursion stops. Other thresholds can also be used. If the process of recursion is not complete, then recursion continues, beginning again with step 2300.

If the process of recursion is complete, then the process returns to step 2330. Thus, the system determines whether additional data is received at step 2330 during the recursion process in steps 2300 through 2324 and after the recursion process is completed at step 2328. If additional data is received, then the system conforms the additional data to the database (step 2332), as described with respect to FIG. 18. The system also associates metadata and a key with each additional datum (step 2334). A key uniquely identifies an individual datum. A key can be any unique identifier, such as a series of numbers, alphanumeric characters, other characters, or other methods of uniquely identifying objects.

If the system determines that additional data has not been received at step 2330, or after associating metadata and a key with each additional datum in step 2334, then the system determines whether to modify the recursion process (step 2336). Modification of the recursion process can include determining new sets of rules, expanding the search space, performing additional recursions after recursions were completed at step 2328, or continuing the recursion process.

In response to a positive determination to modify the recursion process at step 2336, the system again repeats the determination whether additional data has been received at step 2330 and also performs additional recursions from steps 2300 through 2324, as described with respect to step 2326.

Otherwise, in response to a negative determination to modify the recursion process at step 2336, the system determines whether to execute a new query (step 2338). The system can decide to execute a new query based on an inference derived at step 2312, or can execute a new query based on a prompt or entry by a user. If the system executes a new query, then the system can optionally continue recursion at step 2326, begin a new query recursion process at step 2300, or perform both simultaneously. Thus, multiple query recursion processes can occur at the same time. However, if no new query is to be executed at step 2338, then the process terminates.

Thus, the illustrative embodiments provide for creating and using a centralized database for managing information. The centralized database can be used to derive probabilities of inferences based on comparison of data within the centralized database according to a set of search rules. The centralized database can further be used to prioritize the probabilities of the inferences and present the probabilities of the inferences to a user according to the prioritization. The search rules are, themselves, determined by a set of determination rules. Thus, the system prevents the entirety of the data in the database from being compared in every possible combination in order that limited computing resources can execute desired queries. The system is particularly useful in the context of criminal investigations or intelligence services where vast quantities of data are to be sifted. The system is capable of taking in vast quantities of divergent data and accurately producing probabilities of inferences based on the divergent data. If possible, as much information regarding each datum is stored as metadata associated with the corresponding datum. Thus, for example, the source, channel, time of creation, time of modification, time of ownership, ownership, Internet address, whether data is encrypted, encryption methods, and many other forms of information can be stored as metadata associated with each datum. In addition, the metadata associated with each datum is fully searchable and is part of the database search during execution of a query.

Additionally, the illustrative embodiments provide for a novel class of probabilistic inference engines with supporting data structures. Thus, the illustrative embodiments have numerous applications in fields other than generating probabilities of inferences regarding criminal or security issues regarding persons, places, events, and other issues. For example, the methods and devices described herein can be used to perform privacy and security filtering based on significance levels of data. Thus, data can be made accessible to individuals of different security access clearances based on the probabilities of inferences. Accordingly, a higher or lower threshold of certainty with regard to an inference could be required in order for specific data to be made available to the individuals who are making queries or otherwise manipulating the data. Thus, some measure of privacy can be guaranteed using the methods and devices described herein. Similarly, the methods and devices described herein can be used to ensure compliance with medical privacy laws, such as, for example, HIPPA.

In another illustrative example, the methods and devices described herein can be used to create probabilities of inferences relating to drugs and drug testing. For example, the illustrative embodiments can be used to generate probabilities of inferences regarding secondary drug effects over time. Such studies are particularly useful with respect to phase IV drug testing trials involving large numbers of patients. Thus, for example, potentially harmful but difficult to detect side effects of drugs could be detected more quickly using the mechanisms of the present invention. Similarly, potentially beneficial but difficult to detect side effects of drugs could be detected more quickly using the mechanisms of the present invention.

Thus, the illustrative embodiments can be used to determine probabilities of inferences relating to drugs and further relating to testing of drugs, identifying unknown side effects of drugs, identifying new uses for drugs, and/or identifying drugs as being useful for treating a pre-selected medical condition. In the latter case, a pre-selected disease can be identified and the entire field of drugs and disease related information can be compared in order to identify probabilities that one or more drugs would be useful in treating the pre-selected disease.

Additionally, the illustrative embodiments can be used to determine probabilities of inferences relating to identifying at least one interaction of the drug with at least one additional drug. Drugs can have complex interactions that are not easily identified, and a vast number of drugs exist. Thus, the illustrative embodiments are particularly useful for identifying drug interactions. Similarly, the illustrative embodiments can be used to determine probabilities of inferences relating to identifying at least one interaction of the drug with at least one environmental factor. Similarly, the illustrative embodiments can be used to determine probabilities of inferences relating to identifying at least one interaction of the drug with a combination of at least one additional drug, food, and at least one environmental factor.

Moreover, the illustrative embodiments can be used to determine probabilities of inferences relating to identifying an efficacy of the drug. As used herein, an efficacy of a drug can relate to how well a drug performs for its intended purpose or for a newly discovered purpose.

In another illustrative example, the methods and devices described herein can be used to discover biological pathways. A biological pathway is any chain of connected biological functions. Thus, for example, in complex biological processes, pathways, chains of complex reactions, or chains of events could be discovered. Similarly, in another illustrative example, the methods and devices described herein can be used to define the interaction of known or newly discovered biological pathways and the environment.

Thus, for example, a probability of an inference can be related to an interaction between a biological pathway or a biological system and an environmental factor. Examples of biological systems are the nervous system, the digestive system, symbiotic systems between cells, systems within cells and organelles, and possibly also life cycle systems among a vast number of organisms. Environmental factors can be any factor external to the biological system but that somehow is related to or interacts with the biological system. Examples of environmental factors include but are not limited to quantifiable factors, such as temperature, pH, and other measurable quantities, and factors for which a subjective value can be placed, such as security, comfort, and others.

Additionally, the illustrative embodiments can be used to create inferences regarding a relationship between a biological pathway and at least one of a drug, a food, a substance interacting with the biological pathway, a gene, an environmental factor, and combinations thereof. Many different interactions can occur between these factors. In one example, an interaction between statin drugs and grapefruit juice was discovered after laborious study. The illustrative embodiments can be used to identify probabilities of inferences of similar such interactions.

Similarly, affects and proximal affects of biological systems, pathways, environments, and their interactions can be identified. An affect is a direct affect of a biological system, an environment, or an interaction thereof. A proximal affect is some fact or condition that results in the direct affect or in a chain of additional proximal affects that leads to the direct affect of the biological system, environment, or an interaction thereof. Note that biological systems can have an impact on an environment, leading to potentially very complex interactions as the change in environment in turn leads to additional changes in the biological systems.

In another illustrative example, the methods and devices described herein can be used with respect to chaotic events and issues relating to a chaotic event. As used herein, the term "relating to a chaotic event" means any fact, person, or object that can be connected to the chaotic event, however tangentially.

For example, an illustrative embodiment can be used to determine a cause of a chaotic event or a proximal cause of a chaotic event. A cause is a direct cause of a chaotic event. A proximal cause is some fact or condition that results in the direct cause or in a chain of additional proximal causes that leads to the direct cause of the chaotic event. For example, probability of a cause of a fire might be determined, along with proximal causes of that fire. In a specific example, a faulty wire might be a cause of the fire and an electrical surge a proximal cause. These facts are all part of a vast plurality of data that might be gathered and then processed by the illustrative embodiments.

Another illustrative embodiment can be used to determine an affect of a chaotic event. For example, a house is destroyed in a hurricane. Through the use of the illustrative embodiments a probability can be determined that the house was actually destroyed by a gas explosion. An affect of the hurricane could be the felling of a tree, and the felling of the tree broke a gas main, and the broken gas main lead to an explosion after a spark from an electrical surge. Thus, the illustrative embodiments can be used to track affects and proximal affects of events such as a hurricane or other chaotic events. Similarly, in the illustrative embodiments, the probability of the first inference can be used to identify one of an affect of the chaotic event, a proximal event of the chaotic event, and a combination thereof.

Examples of chaotic events include an explosion, a shooting, a gun battle, deployment of a weapon of mass destruction, a storm, a hurricane, a tornado, an earthquake, a volcanic eruption, an impact of an extraterrestrial object, a fire, a flood, a tidal wave, a toxic spill, a nuclear meltdown, an infestation of insects, a plague, a disruption of communication systems, a disruption of the Internet, a disruption of economic systems, a riot, an incidence of food poisoning, a mud slide, a rock slide, an avalanche, and combinations thereof. However, may other types of chaotic events exist to which the illustrative embodiments are applicable.

Additionally, the illustrative embodiments are useful for using the probability inferences to assign administration of aid in response to the chaotic event. Generally, aid can be any type of aid, including humanitarian aid, assignment of resources, assignment of personnel to particular problems or areas, or any other type of aid. In an example, the illustrative embodiments can be used to assign aid in response to massive chaotic events, such as Hurricane Katrina. Moreover, the illustrative embodiments can be used to define scored conditions in a mass casualty situation. For example, after a major disaster, such as Hurricane Katrina, the methods and mechanisms of the present invention can be used to track and administer disaster relief as well as probabilities of inferences of where related disasters (such as levy breaches) might occur and where and how to respond. The present invention can also apply to other disaster management processes.

In another illustrative example, similar to the above example relating to chaotic events, the methods and devices described herein can also be applied to accident investigation, particularly complex accident investigation. For example, after an airplane crash, potentially thousands or even millions of parts of an airplane or of passenger remains might be recovered and classified. The present invention can be used to generate, for example, probabilities of inferences of a cause or multiple causes of the accident based on available data. Once accident causes are suspected, the mechanisms of the present invention can be used to create probabilities of inferences that other, similar risks exist in other aircraft. Thus, remedial action can be taken to prevent future similar accidents.

Non-limiting examples of accidents to which the illustrative embodiments can be applied an airplane accident, a train accident, a multi-vehicle accident, a maritime accident, a single vehicle accident, a nuclear meltdown, a black-out, a building collapse, a failure of a bridge, a failure of a dam, a toxic spill, an explosion, and combinations thereof. The illustrative embodiments can be applied to other accidents.

In addition to investigating the cause of accidents, the illustrative examples can be used to assist in administering aid after an accident and in identifying a cause or proximal cause of an accident. A cause of an accident is a direct cause of the accident. A proximal cause of an accident is some fact or condition that results in the direct cause or in a chain of additional proximal causes that leads to the direct cause of the accident. Thus, the illustrative embodiments can be used to identify one of a cause of the accident, a proximal cause of the accident, and a combination thereof. Additionally, probability of an inference can be used to assign administration of aid in response to the accident.

In another illustrative example, the methods and devices described herein can be used with respect to clinical applications. For example, the illustrative embodiments can be used to discover unobtrusive or difficult to detect relationships in disease state management. Thus, for example, the present invention can be used to track complex cases of cancer or multiply interacting diseases in individual patients. Additionally, patterns of a disease among potentially vast numbers of patients can be inferred in order to detect facts relating to one or more diseases. Furthermore, perhaps after analyzing patterns of a disease in a vast number of patients treated according to different treatment protocols, probabilities of success of various treatment plans can be inferred for a particular plan. Thus, another clinical application is determining a treatment plan for a particular patient.

In another clinical application, the methods and devices described herein can also be used to perform epidemic management and/or disease containment management. Thus, for example, the present invention can be used to monitor possible pandemics, such as the bird flu or possible terrorist activities, and generate probabilities of inferences of an explosion of an epidemic and the most likely sites of new infections.

In another clinical application, the methods and devices described herein can be used to perform quality control in hospitals or other medical facilities to continuously monitor outcomes. In particular, the methods and devices described herein can be used to monitor undesirable outcomes, such as hospital borne infections, re-operations, excess mortality, and unexpected transfers to intensive care or emergency departments.

In another clinical application, the methods and devices described herein can be used to perform quality analysis in hospitals or other medical facilities to determine the root causes of hospital borne infections. For example, wards, rooms, patient beds, staff members, operating suites, procedures, devices, drugs, or other systematic root causes, including multiple causalities can be identified using the methods and devices described herein.

Quality analysis in hospitals, medical facilities, doctors' offices, dentist offices, or other healthcare settings is becoming increasingly important. For example, the U.S. Department of Health and Human Services has specific reporting requirements for hospitals regarding healthcare quality measures. These quality measures are used in governmental reporting and are posted on governmental websites. Given the availability of information, healthcare providers are even more keenly interested in identifying causes or proximal causes of unsatisfactory patient outcomes in order to provide better service, reduce patient mortality, increase quality of patient services and recovery, and decrease liability. A cause is a direct cause of a healthcare outcome. A proximal cause is some fact or condition that results in the direct cause or in a chain of additional proximal causes that leads to the direct cause of the healthcare outcome.

On the other hand, healthcare providers are also keenly interested in identifying causes of satisfactory patient outcomes. Thus, healthcare providers can increase patient survival and improve the quality and length of patient recovery, while simultaneously reducing the cost of providing healthcare services.

State of the art investigation of healthcare setting quality assurance provides that an investigator investigate one or more outcomes and work back to a single root cause of those outcomes. This single root cause orientation is often successful in discovering the most significant problem in a chain of events that led to an outcome. However, analyzing the relationships among thousands or even millions of facts to produce chains of causations has proved to be impossible.

Using the methods and devices described herein, a network of interlinking chains of occurrences and the probability of various outcomes at each node of the network can be determined. The probability distribution functions of specific outcomes can be expressed as single point estimates, low-medium-high probability estimates, and mathematical equations representing probability distribution functions of outcomes. Multiple distinct outcomes can be expressed at each node as well as their associated probability distribution function. The network of occurrences can be cross-linked between the causal relationships of different networks.

In an illustrative example, a budgetary restriction causes a reduction in the training of maintenance persons who clean and sterilize operating theaters. Surgical operating room theaters may be totally sterile, may have minimal contamination, or may have heavy contamination as a result. The operating room can be contaminated with gram positive organisms, gram negative organisms, or drug resistant organisms. Each of these combinations of sterile or contaminated operating rooms have a probability of occurrence. Thus, for example, the operating room can have a heavy contamination of gram negative organisms and a light contamination of drug resistant organisms.

Continuing the example, a patient scheduled for surgery in that particular operating room does not receive antibiotic treatment before the scheduled surgical procedure because the treatment is not ordered. The probability of this occurrence could be low, but positive.

During the scheduled procedure, assuming the presence of organisms, the patient's open incision may not be contaminated or may be contaminated with one or more organisms. Thus, for example, the operating room could be heavily contaminated with several organisms and the patient could escape infection.

If the patient had received a prophylactic antibiotic treatment and the organism is not drug resistant, a probability exists that the patient will or will not be seriously infected. A probability exists that the patient was infected, the antibiotic was effective and the patient never showed any sign of serious infection. The patient may be infected and take 4, 8, 12, 16, 20, or 24 hours to beat the infection with associated probabilities that the infection was beaten in a given number of hours or sooner. The probabilities would be expressed as a cumulative probability distribution function over the set of timings.

The patient could be infected with a drug resistant organism even if the patient received the prophylactic antibiotic treatment. The organism could be defeated by the patient's own immune system within 4, 8, 12, 24, 36, 48, or 60 hours. Alternately the doctor could note the infection and change the antibiotic to one or more of the little used backup antibiotics. The patient then has some probability of responding to treatment or dying. Alternately, a probability exists that the doctor will not change the antibiotic, resulting in the one of two events: that the patient lives or dies.

Staffing levels on the nursing staff can have a significant impact on the probabilities of noticing and beginning prompt treatment of infections. Lack of staff due to inability to hire enough nurses, nurses leaving this hospital to another hospital in the local area which provides a more favorable employment environment, or lack of funding for infection control in-service training can each play a role in changing the probabilities of bad outcomes. A poor employment environment is not often cited as a major cause of hospital borne infection, but that relationship could be ignored in a typical Bayesian decision tree or fish bone causality chart as used in the known art. The methods and devices described herein take into account seemingly unrelated factors such as poor employment environment in determining chains of causation of an outcome. In the illustrative examples, the causes of bad outcomes are the result of complex webs of interrelationships that can be modeled as a network of interactions.

Thus, the illustrative examples provide for a computer implemented method for inferring a probability of a first inference related to identification of a cause of an outcome in a healthcare setting. The method includes receiving a query at a database regarding a fact related to the healthcare setting. The fact further relates to a network of interactions associated with the outcome. The first inference is absent from the database. The database includes a plurality of divergent data. The plurality of divergent data includes a plurality of cohort data. Each datum of the database is conformed to the dimensions of the database. Each datum of the plurality of data has associated metadata and an associated key. The associated metadata comprises data regarding cohorts associated with the corresponding datum, data regarding hierarchies associated with the corresponding datum, data regarding a corresponding source of the datum, and data regarding probabilities associated with integrity, reliability, and importance of each associated datum. The method further includes establishing the fact as a frame of reference for the query. The method further includes applying a first set of rules to the query. The first set of rules are determined for the query according to a second set of rules. The first set of rules determine how the plurality of data are to be compared to the fact. The first set of rules determine a search space for the query. The method further includes executing the query to create the probability of the first inference. The probability of the first inference is determined from comparing the plurality of data according to the first set of rules. The method further includes storing the probability of the first inference.

In an illustrative example the outcome is an undesirable outcome and the cause is a root cause of the undesirable outcome. An undesirable outcome is any outcome deemed undesirable by a human. A cause can be any cause, including a proximal cause as described above. For example, the proximal cause can be at least one of training of personnel, presence of personnel, unavailability of trained personnel, presence of equipment, absence of equipment, an unsatisfactory working environment, a budgetary restriction, a human error, presence of a bacterium, presence of a virus, contamination of an area of the healthcare setting, failure to administer a drug to at least one patient, failure to administer a drug to the patient for a long enough time, failure to administer a combination of drugs, failure to administer a combination of drugs to the at least one patient for a long enough time, failure to administer a treatment to the at least one patient, failure to administer a plurality of treatments to the at least one patient, administration of a procedure on the at least one patient, administration of a combination of procedures on the at least one patient, administration of a drug to the at least one patient, administration of a combination of drugs to the at least one patient, scheduling of administration of procedures, scheduling of administration of drugs, and combinations thereof. Any of these proximal causes can be a root cause. Some of these causes, such as budgetary constraints, can only be proximal causes. Other of these causes can be direct causes, such as contamination or a bacterium.

Alternatively, the outcome can be a desirable outcome. A desirable outcome is any outcome deemed desirable by a human being. In an illustrative example, a desirable outcome is patient recovery. A cause of a desirable outcome could be at least one of training of personnel, presence of personnel, presence of equipment, absence of equipment (from a cost perspective), a working environment having pre-defined characteristics, an allocation of funds, a human error that results in a positive outcome, presence of a bacterium that results in a positive outcome, presence of a virus that results in a positive outcome, decontamination of an area of the healthcare setting, failure to administer a drug to at least one patient such that a favorable positive results, failure to administer a drug to the patient for a long enough time such that a favorable positive results, failure to administer a combination of drugs such that a favorable positive results, failure to administer a combination of drugs to the at least one patient for a long enough time such that a favorable positive results, failure to administer a treatment to the at least one patient such that a favorable positive results, failure to administer a plurality of treatments to the at least one patient such that a favorable positive results, administration of a procedure on the at least one patient, administration of a combination of procedures on the at least one patient, administration of a drug to the at least one patient, administration of a combination of drugs to the at least one patient, scheduling of administration of procedures, scheduling of administration of drugs, and combinations thereof.

In an illustrative example, the method described above can further include expressing a specific outcome as at least one probability distribution function. The at least one probability distribution function includes a single point probability estimate, a low-medium-high probability estimate, and a mathematical equation representing a probability distribution function of at least one outcome. In this case, the method can further include expressing a number of outcomes as at least one corresponding probability distribution function expressed at each node of the network of interactions.

In an illustrative example, the method described above can further include cross-linking a network of outcomes to the network of interactions. Additionally, this method can further include establishing a network of causations among the network of outcomes and the network of interactions. Additionally, the method can include establishing a plurality of probabilities of corresponding causations in the network of causations at each node of network of interactions.

In another clinical application, the methods and devices described herein can be used to determine a cause of a disease or a proximal cause of a disease. A cause is a direct cause of a disease. A proximal cause is some fact or condition that results in the direct cause or in a chain of additional proximal causes that leads to the direct cause of the disease. Thus, for example, a complex interplay of genetics, environmental factors, and lifestyle choices can be examined to determine a probability that one or more factors or combinations of factors causes a disease or other medical condition.

In another clinical application, the methods and devices described herein can be used for monitoring public health and public health information using public data sources. For example, the overall purchasing of over-the-counter drugs can be monitored. People are likely to self-medicate when they become sick, seeking medical attention only if they become very ill or the symptoms of an illness don't abate. Thus, a spike in purchase of over-the-counter drugs in a particular geographical location can indicate a possible public health problem that warrants additional investigation. Possible public health problems include natural epidemics, biological attacks, contaminated water supplies, contaminated food supplies, and other problems. Additional information, such as specific locations of excessive over-the-counter drug purchases, time information, and other information can be used to narrow the cause of a public health problem. Thus, public health problems can be quickly identified and isolated using the mechanisms described herein.

A summary of clinical applications, therefore includes determining a cause of a disease, determining a proximal cause of a disease, determining a cause of a medical condition, determining a proximal cause of a medical condition, disease state management, medical condition management, determining a pattern of at least one disease in a plurality of patients, determining a pattern of at least one medical condition in a plurality of patients, selecting a treatment plan for a particular patient, determining a genetic factor in relation to a disease, determining a genetic factor in relation to a medical condition, epidemic management, disease containment management, quality control in a medical facility, quality analysis in the medical facility, and monitoring public health. A medical condition is any condition from which a human or animal can suffer which is undesirable but which is not classified as a disease.

In another illustrative example, the methods and devices described herein can be used to perform defect analysis for low frequency, high impact defects. A low frequency defect is a defect that manifests itself relatively infrequently. A high impact defect is a defect that results in some kind of relatively catastrophic result or high impact effect on a system. For example, a particular tire manufactured by a particular manufacturer might be prone to failure when installed on a particular type of chassis, but only in hot weather conditions. The defect of tire blow-out might occur infrequently because of the required confluence of events, but the impact of the defect can be high as a potentially serious automobile accident can result. The present invention can be used to generate probabilities of inferences that a low frequency, high impact defect exists.

In another illustrative example, the methods and devices described herein can be used for battle management augmentation. Battles, from small firefights to large scale engagements, are subject to rapidly changing conditions. Commanders must make decisions very quickly based on available information. Available information can be a great deal of information, given modern information gathering techniques used in modern battle management, though the information might be incomplete or vague. The illustrative embodiments can be used to manage the potentially vast amount of information available to aid commanders in making decisions during battle.

In another illustrative example, the methods and devices described herein can be used to perform geo-economic impact analysis. In geo-economic impact analysis, a comparison is made among changes in environment to changes in quality of life and local economics. Geo-economic impact analysis is especially useful in urban environments. For example, how does the quality of life in an urban environment change when several windows are broken, but unrepaired. In another example, changes in quality of life can be analyzed based on which laws governing minor infractions are enforced.

In another illustrative example, the methods and devices described herein can be used to monitor employee retention for hard-to-fill jobs such as nursing jobs, laboratory technician jobs, radiologist jobs, legal jobs, executive jobs, or any other job in which a high degree of expertise is required. For example, compensation packages, working conditions, working environment, perquisites, work hours, stress, skills, work habits, personal habits, and other factors can be compared in order to determine which overall combinations of work environments and compensation packages will most likely result in maximum employee retention.

In another illustrative example, the methods and devices described herein can be used to monitor gangs and gang related activities. For example, the detailed social structures of gangs can be tracked, including hierarchies, members, propensity to various illegal activities, and the recruitment techniques for attracting new members. Thus, the methods and devices described herein can be used to both track and deter criminal gangs, but also to limit new recruits for criminal gangs.

In another illustrative example, the methods and devices described herein can be used by human resource departments in medium to large organizations to determine individual level skills by examination of participation in sales opportunities. This type of data collection can be performed by a variety of known software packages, such as Siebel, a customer relationship management software package available from Oracle Corporation. The methods and devices described herein can use information acquired by Siebel, manual data input, and other sources to determine the relative success of individuals on classes of sales opportunities. This analysis would also show gaps in skills that should be addressed by training existing employees or by hiring additional employees with the desired skills.

In another illustrative example, the methods and devices described herein can be used to monitor tax advisors and tax payers for patterns of tax fraud. For example, the relationships between individuals who do not pay taxes, tax preparers and other individuals, locations, and times can be used to generate inferences regarding specific tax preparers and tax avoidance transactions. This information can be used to determine cohorts of tax payers relying on similar tax avoidance schemes. Thus, the methods and devices described herein can be used to identify tax fraud, aid prosecution of those who commit tax fraud, and potentially increase tax revenue.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method for inferring a probability of a first inference related to identification of a cause of an outcome in a healthcare setting, the computer implemented method comprising:

receiving a query at a database regarding a fact related to the healthcare setting, wherein the fact further relates to a network of interactions associated with the outcome, wherein the first inference is absent from the database, wherein the database comprises a plurality of divergent data, wherein the plurality of divergent data includes a plurality of cohort data, wherein each datum of the database is conformed to the dimensions of the database, wherein each datum of the plurality of data has associated metadata and an associated key, wherein the associated metadata comprises data specifying cohorts associated with the corresponding datum, data specifying hierarchies associated with the corresponding datum, data specifying a corresponding source of the datum, and data specifying probabilities associated with integrity, reliability, and importance of each associated datum;

establishing the fact as a frame of reference for the query;

applying a first set of rules to the query, wherein the first set of rules are determined for the query according to a second set of rules, wherein the first set of rules determine how the plurality of data are to be compared to the fact, and wherein the first set of rules determine a search space for the query;

executing the query to create the probability of the first inference, wherein the probability of the first inference is determined from comparing the plurality of data according to the first set of rules; and storing the probability of the first inference.

2. The computer implemented method of claim 1 wherein the outcome is an undesirable outcome and wherein the cause is a root cause of the undesirable outcome.

3. The computer implemented method of claim 1 wherein the outcome is an undesirable outcome, wherein the cause is a proximal cause, and wherein the cause comprises at least one of training of personnel, presence of personnel, unavailability of trained personnel, presence of equipment, absence of equipment, an unsatisfactory working environment, a budgetary restriction, a human error, presence of a bacterium, presence of a virus, contamination of an area of the healthcare setting, failure to administer a drug to at least one patient, failure to administer a drug to the patient for a long enough time, failure to administer a combination of drugs, failure to administer a combination of drugs to the at least one patient for a long enough time, failure to administer a treatment to the at least one patient, failure to administer a plurality of treatments to the at least one patient, administration of a procedure on the at least one patient, administration of a combination of procedures on the at least one patient, administration of a drug to the at least one patient, administration of a combination of drugs to the at least one patient, scheduling of administration of procedures, scheduling of administration of drugs, and combinations thereof.

4. The computer implemented method of claim 3 wherein one of the at least one cause comprises a root cause of the undesirable outcome.

5. The computer implemented method of claim 1 wherein the outcome comprises a desirable outcome.

6. The computer implemented method of claim 5 wherein the cause comprises at least one of training of personnel, presence of personnel, presence of equipment, absence of equipment, a working environment having pre-defined characteristics, an allocation of funds, a human error, presence of a bacterium, presence of a virus, decontamination of an area of the healthcare setting, failure to administer a drug to at least one patient, failure to administer a drug to the patient for a long enough time, failure to administer a combination of drugs, failure to administer a combination of drugs to the at least one patient for a long enough time, failure to administer a treatment to the at least one patient, failure to administer a plurality of treatments to the at least one patient, administration of a procedure on the at least one patient, administration of a combination of procedures on the at least one patient, administration of a drug to the at least one patient, administration of a combination of drugs to the at least one patient, scheduling of administration of procedures, scheduling of administration of drugs, and combinations thereof.

7. The computer implemented method of claim 6 further comprising:

executing a second query to create a second probability of a second inference, wherein the second probability of the second inference is determined from comparing the plurality of data according to the set of rules.

8. The computer implemented method of claim 1 further comprising:

responsive to receiving an additional datum in the database, establishing a second query;

applying a third set of rules to the query, wherein the third set of rules are determined for the second query according to a fourth set of rules, and wherein the third set of rules determine how the plurality of data are to be compared to the fact; and executing the second query to create a second probability of a second inference, wherein the second probability of the second inference is determined from comparing the plurality of data according to the third set of rules.

9. The computer implemented method of claim 1 further comprising:

expressing a specific outcome as at least one probability distribution function.

10. The computer implemented method of claim 9 wherein the at least one probability distribution function comprises at least one of a single-point probability estimate, a low-medium-high probability estimate, and a mathematical equation representing a probability distribution function of at least one outcome.

11. The computer implemented method of claim 10 further comprising expressing a plurality of outcomes as at least one corresponding probability distribution function expressed at each node of the network of interactions.

12. The computer implemented method of claim 1 further comprising:

cross-linking a network of outcomes to the network of interactions.

13. The computer implemented method of claim 12 further comprising:

establishing a network of causations among the network of outcomes and the network of interactions.

14. The computer implemented method of claim 13 further comprising:

establishing a plurality of probabilities of corresponding causations in the network of causations at each node of the network of interactions.

15. The computer implemented method of claim 1 wherein the set of rules includes rules for adjusting the probability of the inference based on background data.

16. A database stored in a recordable-type medium, wherein the database is related to identification of a cause of an outcome in a healthcare setting, the database comprising:

a plurality of divergent data stored in a data structure on the recordable-type medium, wherein the plurality of divergent data includes a plurality of cohort data, wherein each datum of the database is conformed to the dimensions of the database, wherein each datum of the plurality of data has associated metadata and an associated key, wherein the associated metadata comprises data specifying cohorts associated with the corresponding datum, data specifying hierarchies associated with the corresponding datum, data specifying representing a corresponding source of the datum, and data specifying probabilities associated with integrity, reliability, and importance of each associated datum;

computer usable program code for establishing a fact related to the healthcare setting, wherein the fact further relates to a network of interactions associated with the outcome, received in a query, as a frame of reference for the query;

computer usable program code for applying a first set of rules to the query, wherein the first set of rules are determined for the query according to a second set of rules, wherein the first set of rules determine how the plurality of data are to be compared to the fact, and wherein the first set of rules determine a search space for the query;

computer usable program code for executing the query to create a probability of a first inference, wherein the probability of the first inference is determined from comparing the plurality of data according to the first set of rules; and computer usable program code for storing the probability of the first inference.

17. The database of claim 16 wherein the outcome is an undesirable outcome and wherein the cause is a root cause of the undesirable outcome.

18. The database of claim 16 wherein the outcome is an undesirable outcome and wherein the cause comprises at least one of training of personnel, presence of personnel, unavailability of trained personnel, presence of equipment, absence of equipment, an unsatisfactory working environment, a budgetary restriction, a human error, presence of a bacterium, presence of a virus, contamination of an area of the healthcare setting, failure to administer a drug to at least one patient, failure to administer a drug to the patient for a long enough time, failure to administer a combination of drugs, failure to administer a combination of drugs to the at least one patient for a long enough time, failure to administer a treatment to the at least one patient, failure to administer a plurality of treatments to the at least one patient, administration of a procedure on the at least one patient, administration of a combination of procedures on the at least one patient, administration of a drug to the at least one patient, administration of a combination of drugs to the at least one patient, scheduling of administration of procedures, scheduling of administration of drugs, and combinations thereof.

19. The database of claim 18 further comprising:
computer usable program code for cross-linking a network of outcomes to the network of interactions.

20. The database of claim 19 further comprising:
computer usable program code for establishing a network of causations among the network of outcomes and the network of interactions; and computer usable program code for establishing a plurality of probabilities of corresponding causations in the network of causations at each node of network of interactions.

* * * * *